United States Patent
Leinwand et al.

(10) Patent No.: US 9,925,162 B2
(45) Date of Patent: Mar. 27, 2018

(54) METHODS AND COMPOSITIONS FOR INDUCING PHYSIOLOGICAL HYPERTROPHY

(75) Inventors: Leslie A. Leinwand, Boulder, CO (US); Cecilia Riquelme, Santiago (CL); Brooke Harrison, Boulder, CO (US); Jason Magida, Boulder, CO (US)

(73) Assignee: THE REGENTS OF THE UNIVERSITY OF COLORADO, Denver, CO (US)

(*) Notice: Subject to any disclaimer, the term of this patent is extended or adjusted under 35 U.S.C. 154(b) by 0 days.

(21) Appl. No.: 13/263,699

(22) PCT Filed: Apr. 9, 2010

(86) PCT No.: PCT/US2010/030591
§ 371 (c)(1),
(2), (4) Date: Dec. 19, 2011

(87) PCT Pub. No.: WO2010/118362
PCT Pub. Date: Oct. 14, 2010

(65) Prior Publication Data
US 2012/0101162 A1 Apr. 26, 2012

Related U.S. Application Data

(60) Provisional application No. 61/168,060, filed on Apr. 9, 2009.

(51) Int. Cl.
*A61K 31/20* (2006.01)
(52) U.S. Cl.
CPC .................................. *A61K 31/20* (2013.01)

(58) Field of Classification Search
None
See application file for complete search history.

(56) References Cited

U.S. PATENT DOCUMENTS

| | | | |
|---|---|---|---|
| 4,083,949 A | 4/1978 | Benedikt | 424/459 |
| 4,474,773 A | 10/1984 | Shinitzky et al. | 514/78 |
| 4,874,795 A | 10/1989 | Yesair | 514/725 |
| 5,198,250 A | 3/1993 | Brillhart et al. | 426/2 |
| 5,578,334 A | 11/1996 | Sundram et al. | |
| 5,648,380 A | 7/1997 | Martin | 514/461 |
| 5,843,497 A | 12/1998 | Sundram et al. | |
| 6,313,167 B1 | 11/2001 | Nakajima et al. | |
| 6,506,377 B2 | 1/2003 | Cummins et al. | 424/85.7 |

(Continued)

FOREIGN PATENT DOCUMENTS

CN 1212867 4/1999
WO WO 2007070307 A2 * 6/2007

OTHER PUBLICATIONS

Ahn et al. "Fatty Acids Directly Increase the Activity of Ca2+-activated K+ Channels in Rabbit Coronary Smooth Muscle Cells" Yonsei Medical Journal. 1994; 35(1):10-24.*

(Continued)

*Primary Examiner* — Marcos L Sznaidman
*Assistant Examiner* — Rayna Rodriguez
(74) *Attorney, Agent, or Firm* — Cooley LLP

(57) ABSTRACT

Methods and compositions are provided for inducing physiologic hypertrophy in a cell for treatment or prevention of a cardiovascular disease or condition. In certain embodiments methods and compositions involve an aquaporin 7 inducer.

11 Claims, 11 Drawing Sheets

Serum from fed snake induces cardiac cell hypertrophy

(56) References Cited

U.S. PATENT DOCUMENTS

| | | |
|---|---|---|
| 7,192,951 B2 | 3/2007 | Bakker-Arkema et al. ... 514/215 |
| 7,262,221 B2 | 8/2007 | Uhrich |
| 7,439,267 B2 | 10/2008 | Granata et al. |
| 7,612,111 B2 | 11/2009 | Spencer et al. |
| 7,776,914 B2 | 8/2010 | Spencer |
| 8,057,825 B2 | 11/2011 | Sampalis |
| 2005/0186290 A1 | 8/2005 | Cals-Grierson ............ 424/725 |
| 2005/0208162 A1* | 9/2005 | Spencer et al. ............ 424/769 |
| 2006/0052351 A1 | 3/2006 | Platt et al. |
| 2006/0228429 A1 | 10/2006 | Laguna Granja et al. ... 424/727 |
| 2007/0009474 A1 | 1/2007 | Xie et al. .................... 424/74 |
| 2007/0118929 A1 | 5/2007 | Damude et al. ............ 800/281 |
| 2007/0203083 A1 | 8/2007 | Mootha et al. ............ 514/44 R |
| 2008/0175957 A1* | 7/2008 | Horgan et al. ............. 426/73 |
| 2008/0221169 A1 | 9/2008 | Flynn et al. ................ 514/351 |
| 2009/0209757 A1 | 8/2009 | Ini et al. |
| 2009/0270502 A1 | 10/2009 | Sundram et al. ........... 514/558 |
| 2010/0021555 A1 | 1/2010 | Geiringer et al. |
| 2010/0130608 A1 | 5/2010 | Ryan et al. |
| 2010/0285105 A1 | 11/2010 | Radianingtyas |
| 2011/0008396 A1 | 1/2011 | Moghe et al. |
| 2011/0195128 A1 | 8/2011 | Palmano et al. |
| 2011/0206741 A1 | 8/2011 | Lee et al. |
| 2012/0022159 A1 | 1/2012 | Uhrich et al. |

OTHER PUBLICATIONS

Pang et al. "High-conductance, Ca2+-activated K+ Channels: Altered Expression Profiles in Aging and Cardiovascular Disease" Molecular Interventions, 2009; 9(5):230-233.*

Clarke et al ("Modulation of BKCa channel activity by fatty acids: structural requirements and mechanism of action" Am J Physiol Cell Physiol, 2002; 283:C1441-C1453).*

Dorn, "The Fuzzy Logic of Physiological Cardiac Hypertrophy," *Hypertension* 49:962-970, 2007.

Andersen, et al., "Physiology: postprandial cardiac hypertrophy in pythons," *Nature*. 434:37-38, 2005.

Ceperuelo-Mallafré, et al., "Adipose tissue expression of the glycerol channel aquaporin-7 gene is altered in severe obesity but not in type 2 diabetes," *J. Clin. Endocrinol. Metab.*, 92:3640-5, 2007.

Cup, et al., "Fatty acid-albumin complexes and the determination of the transport of long chain free fatty acids across membranes," *Biochemistry*, 43:4473-81, 2004, abstract only.

de Vries, et al., "Saturated but not mono-unsaturated fatty acids induce apoptotic cell death in neonatal rat ventricular myocytes, " *J. Lipid Res.*, 38:1384-94, 1997.

Duan, et al., "Cardiomyocyte-specific knockout and agonist of peroxisome proliferator-activated receptor-gamma both induce cardiac hypertrophy in mice," *Circ. Res.*, 97:372-9, 2005.

Frigeri, et al., "Aquaporins as targets for drug discovery," *Curr. Pharm. Des.*, 13:2421-7, 2007.

Hara-Chikuma, et al., "Progressive adipocyte hypertrophy in aquaporin-7-deficient mice: adipocyte glycerol permeability as a novel regulator of fat accumulation," *J. Biol. Chem.*, 280:15493-6, 2005.

Hibuse, et al., "The heart requires glycerol as an energy substrate through aquaporin 7, a glycerol facilitator," *Cardiovasc. Res.*, 83:31-41, 2009.

International Search Report and Written Opinion, issued in Application No. PCT/US2010/030591, dated Jul. 20, 2010.

Jamshidi, et al., "Peroxisome proliferator-activated receptor alpha gene regulates left ventricular growth in response to exercise and hypertension," *Circulation*, 105:950-5, 2002.

Riqueleme et al., "Fatty acids identified in the Burmese Python promote beneficial cardiac growth," *Science*, 334(6055):528-531, 2011.

Riquelme, et al., "Pro-hypertrophic factors present in post-prandial python serum: effects on neonatal rat cardiomyocytes," Abstract No. 60.3, *Integrative and Comparative Biology*, 49(Suppl. 1):E144, 2009.

Secor and Diamond, "A vertebrate model of extreme physiological regulation," *Nature*, 395:659-62, 1998.

Takahashia, et al., "Dietary fish oil attenuates cardian hypertrophy in lipotoxic cardiomyopathy due to systemic carnitine deficiency," *Cardiovascular Research*, 68:213-23, 2005.

van der Lee, et al., "Effects of fatty acids on uncoupling protein-2 expression in the rat heart," FASEB J., 14:495-502, 2000.

van der Lee, et al., "Long chain fatty acid-induced changes in gene expression in neonatal cardiac myocytes," *J. Lipid Res.*, 41:41-47, 2000.

Yamori, et al., "Dietary prevention of stroke and its mechanisms in stroke-prone spontaneously hypertensive rats-preventive effect of dietary fibre and palmitoleic acid," *J. Hypertension*, 4:S449-S452, 1986.

Zahabi and Deschepper, "Long-chain fatty acids modify hypertrophic responses of cultured primary neonatal cardiomyocytes," *J. Lipid Res.*, 42:1325-30, 2001.

Guarrasi et al. "Quantification of Underivatized Fatty Acids from Vegetable Oils by HPLC with UV Detection." *J Chromoatogr. Sci.* 2010 vol. 48(8) p. 663-638.

DeBierre-Grockiego et al. "Fatty Acids from Plasmodium falciparum Down-Regulate the Toxic Activity of Malaria Glycosylphosphatidylinositols." *Infect. Immun.* 2006 vol. 74(10) p. 5487-5496.

LeMaitre et al. "Endogenous red blood cell membrane fatty acids and sudden cardiac arrest." *Metabolism* 2010 vol. 59(7), p. 1029-1034.

International Search Report PCT US 2012-41347, dated Dec. 10, 2012; 15 pages.

* cited by examiner

METHODS AND COMPOSITIONS FOR INDUCING PHYSIOLOGICAL HYPERTROPHY

The present application is a national phase application under 35 U.S.C. § 371 of International Application No. PCT/US2010/030591 filed Apr. 9, 2010 which claims the priority benefit of U.S. provisional application No. 61/168,060, filed Apr. 9, 2009 the entire contents of which are incorporated herein by reference.

BACKGROUND

Field of the Invention

The present invention is generally related to molecular biology and cardiology. More specifically, it concerns methods and compositions related to inducing physiologic hypertrophy in a cell, such as a cardiac cell, in therapeutic and preventative applications. In certain embodiments it concerns Aquaporin 7 (AQP-7). In further embodiments it involve methods and compositions that alter AQP-7, such as fatty acids combinations.

Description of Related Art

Cardiac enlargement—more commonly termed cardiac hypertrophy—is a major risk factor of premature cardiovascular morbidity and mortality. In fact, cardiac hypertrophy is the best predictor of mortality. Few drugs are effective in treating the most costly endpoint of these diseases, congestive heart failure. The most commonly used treatments include digoxin, ACE inhibitors, diuretics, and β adrenergic receptor blockade.

Excessive hemodynamic workload (heart attack or high blood pressure), genetic mutations affecting sarcomeric proteins, and alterations in calcium handling proteins are some examples of stimuli that can stress the heart and induce hypertrophy. This is referred to as pathologic hypertrophy. The initial growth of the heart is a compensatory mechanism to alleviate the increased workload and to normalize wall tension. However, if the sustained stimulus is not removed, ventricular dilatation and progression to heart failure occur. The molecular pathways that control the pathologic enlargement of the heart have not yet been fully elucidated. Such molecular events may be potential therapeutic targets for preventing or reversing hypertrophy and subsequent heart failure.

An adaptive growth of the heart also occurs during normal postnatal growth or as a consequence of physical conditioning such as exercise. This physiologic hypertrophy is associated with cardiovascular benefit. Indeed, evidence suggests that physiological cardiac growth induced by exercise may protect against pathological stimuli such as pressure overload.

Burmese pythons (*Python molurus*) are opportunistic ambush predators, adapted to consume large meals at infrequent intervals. As a consequence, pythons exhibit a large regulatory response to the digestion process including an increase in its metabolic rate, nutrient transport and organ mass. It has been determined that the python heart can enlarge up to 60% 2 days post-feeding and it reverts to fasting size very rapidly (Secor and Diamond, 1998). Most other regulatory parameters also return to pre-feeding states. Some aspects of the hypertrophic response in the python's heart were reported by Andersen et al., (2005) These authors determined that the increased mass of the heart does not arise from an increase in the fluid content of the tissue. Moreover, the authors report an increase in the ventricular mRNA levels for cardiac myosin.

There is a need to understand the molecular mechanisms of this physiologic hypertrophy and identify factors that serve as therapeutic and preventative agents for cardiac diseases and conditions involving hypertrophy of cardiac cells.

SUMMARY OF THE INVENTION

In some embodiments there are methods and compositions related to inducing hypertrophy in cells. In particular embodiments, physiologic hypertrophy is induced in cardiac cells or cardiomyocytes.

In some embodiments, there are methods for inducing physiological hypertrophy in a cardiac cell in a subject comprising administering to the subject an effective amount of an aquaporin 7 (AQP7) inducer. In further embodiments, there are methods for inducing physiological cardiac hypertrophy in a patient with hypertension comprising administering to the patient an effective amount of a AQP7 inducer. On additional embodiments, there are methods for treating a patient with symptoms or signs of hypertension comprising administering to the patient an effective amount of a AQP7 inducer. In other embodiments, there are methods for preventing or treating cardiac fibrosis in a patient suspected of having cardiac fibrosis or at risk for cardiac fibrosis comprising administering to the patient an effective amount of a AQP7 inducer.

Embodiments include methods for inducing physiologic hypertrophy in cardiac cells comprising administering to the cardiac cells an effective amount of a pharmaceutical composition comprising an isolated or purified fatty acid composition, wherein the fatty acid composition comprises a combination of myristic acid, palmitic acid, and palmitoleic acid fatty acid (MPP fatty acids).

In certain embodiments there are methods for inducing physiologic hypertrophy in cardiac cells of a patient comprising administering to the cardiac cells an effective amount of a pharmaceutical composition comprising an isolated or purified fatty acid composition, wherein the fatty acid composition comprises a combination of myristic acid, palmitic acid, and palmitoleic acid fatty acid (MPP fatty acids).

Additional embodiments concern methods for treating a subject diagnosed with or at risk for a cardiovascular disease or condition. Specific cardiovascular diseases and conditions are discussed herein. In some embodiments, a subject is administered an effective amount of a pharmaceutical composition. In certain embodiments, the pharmaceutical composition comprises a fatty acid composition, which may or may not be a combination of MPP fatty acids.

Other embodiments involve methods of treating a patient for a cardiovascular disease or condition comprising providing to the patient an effective amount of a pharmaceutical composition comprising an isolated or purified fatty acid composition, wherein the fatty acid composition comprises a combination of myristic acid, palmitic acid, and palmitoleic acid fatty acid (MPP fatty acids).

In some embodiments, methods concern cardiac cells or cardiomyocytes in a subject. In some embodiments, the subject is a mammal. In certain embodiments, the subject is a human patient. In some methods, steps for identifying a subject that may benefit from inducement of physiologic hypertrophy are included. Such steps may involve identifying a subject exhibiting symptoms of a cardiovascular disease or condition or at risk for a cardiovascular disease or condition. Such cardiovascular diseases and conditions are discussed in herein. In some embodiments, methods include analyzing a subject for a cardiovascular disease or condition or symptoms of a cardiovascular disease or condition. Other embodiments may involve performing tests on a subject to evaluate the subject for symptoms of a cardiovascular disease or condition or for increased risk for a cardiovascular disease or condition. In other embodiments, a subject may be evaluated based on the results of tests for symptoms of a cardiovascular disease or condition. The subject may also be evaluated for symptoms or risk based on the taking of a patient history. In some embodiments, a patient is treated with a pharmaceutical composition. This may occur after an evaluation of the patient, after tests are performed on the patients, after results of tests on the patient are obtained, and/or after a diagnosis of the patient with a cardiovascular disease or condition or diagnosis of a significant risk of developing a cardiovascular disease or condition.

Other aspects may include monitoring the patient for symptoms of the cardiovascular disease or condition after the patient has been provided with the pharmaceutical composition. A subject may also be evaluated for cardiovascular improvement following administration of a pharmaceutical composition that induces physiologic hypertrophy.

In specific embodiments, the AQP7 inducer is a pharmaceutical composition comprising a fatty acid combination, which means a combination of at least two different fatty acids. In certain embodiments, a fatty acid composition contains a combination of myristic acid (C:14), palmitic acid (C:16), and palmitoleic acid (C, 16.1) (collectively "MPP fatty acids").

In some embodiments, a pharmaceutical composition and/or fatty acid composition comprises myristic acid, by itself or in combination with other saturated and/or unsaturated fatty acids. In specific embodiments, there are pharmaceutical compositions and/or fatty acid compositions comprising myristic acid in combination with palmitic acid and/or palmitoleic acid. Such compositions may or may not comprise additional saturated and/or unsaturated fatty acids.

In additional embodiments, a pharmaceutical composition and/or fatty acid compositions comprises palmitic acid, by itself or in combination with other saturated and/or unsaturated fatty acids. In specific embodiments, there are pharmaceutical compositions and/or fatty acid compositions comprising palmitic acid in combination with myristic acid and/or palmitoleic acid. Such compositions may or may not comprise additional saturated and/or unsaturated fatty acids.

In further embodiments, a pharmaceutical composition and/or fatty acid compositions comprises palmitoleic acid, by itself or in combination with other saturated and/or unsaturated fatty acids. In specific embodiments, there are pharmaceutical compositions and/or fatty acid compositions comprising palmitoleic acid in combination with palmitic acid and/or myristic acid. Such compositions may or may not comprise additional saturated and/or unsaturated fatty acids.

It is contemplated that the ratio of one fatty acid to a second fatty acid may be about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein.

In a composition with more than two fatty acids, it is contemplated that the ratio of a first fatty acid to a second fatty acid may be what is described in the previous paragraph. In further embodiments, such a composition may have a ratio of the second fatty acid to a third fatty acid, or a ratio of the first fatty acid to a third fatty acid, as follows: about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein. Similarly, in a composition containing more than three fatty acids, it is contemplated that the ratio of a first fatty acid to a second fatty acid may be what is described in the previous paragraph, and the second and third fatty acids as described earlier in this paragraph. In further embodiments, such a composition may have a ratio of the third fatty acid to a fourth fatty acid as follows: about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein.

In specific embodiments, pharmaceutical compositions and/or fatty acid compositions may contain a ratio of myristic acid to palmitic acid that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein. It is contemplated that other fatty acids may or may not be included in this composition. In embodiments in which the composition contains additional components, including but not limited to other fatty acids, the composition may contain a ratio of myristic acid or palmitic acid to another component in the composition that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein.

In specific embodiments, compositions may contain a ratio of myristic acid to palmitoleic acid that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein. It is contemplated that other fatty acids may or may not be included in this composition. In embodiments in which the composition contains additional components, including but not limited to other fatty acids, the composition may contain a ratio of myristic acid or palmitoleic acid to another component in the composition that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein.

In specific embodiments, compositions may contain a ratio of palmitic acid to palmitoleic acid that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein. It is contemplated that other fatty acids may or may not be included in this composition. In embodiments in which the composition contains additional components, including but not limited to other fatty acids, the composition may contain a ratio of palmitic acid or palmitoleic acid to another component in the composition that is about, at least about, or at most about 1:100, 1:95, 1:90, 1:85, 1:80, 1:75, 1:70, 1:65, 1:60, 1:55, 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.75, 1:1.5, 1:1.25, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, and any range derivable therein.

Alternatively, in some embodiments, methods and compositions involve a pharmaceutical composition and/or fatty acid composition that is characterized based on the percentage of a particular fatty acid or a combination of fatty acids. A single fatty acid or combination of fatty acids may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent, or any range derivable therein, of a pharmaceutical composition or fatty acid composition. In certain embodiments, each of or a combination of the following is contained in a pharmaceutical or fatty acid composition: myristic acid, palmitic acid, palmitoleic acid, caprylic acid, lauric acid, tridecanoic acid, pentadecanoic acid, stearic acid, oleic acid, linoleic acid, eicosedienoic acid, eicosatrienoic acid, arachidonic acid, and nervonic acid. Each of these listed fatty acids or a combination of them may constitute about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent, or any range derivable therein, of a pharmaceutical composition or fatty acid composition.

The fatty acid composition is an MPP fatty acid composition. In certain embodiments, the only fatty acids in the fatty acid composition in noncontaminating amounts are myristic acid, palmitic acid, and palmitoleic acid. Alternatively, in some embodiments, the amount of another fatty acid or other fatty acids in a fatty acid composition or pharmaceutical composition containing primarily myristic acid, palmitic acid, and palmitoleic acid (meaning the amount of this combination of fatty acids exceeds the amount of any other fatty acid by itself in the composition) is about or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49% (v/v), or any range derivable therein.

In some embodiments, a fatty acid composition is composed of a combination of MPP fatty acids. In certain embodiments, the amount of the MPP combination of fatty acids in the fatty acid composition is about, at least about, or at most about 5, 10, 15, 20, 25, 30, 35, 40, 45, 50, 55, 60, 65, 70, 75, 80, 85, 90, 95, 100% (v/v), or any range derivable therein. It will be understood that a fatty acid composition refers to a composition of fatty acids. In embodiments in which there is a pharmaceutical composition comprising a fatty acid composition, it will be understood that the components of the fatty acid composition may be mixed or added separately or together to the pharmaceutical composition. In some embodiments, a fatty acid composition consists essentially of myristic acid, palmitic acid, and palmitoleic acid fatty acid.

In certain embodiments, compositions have a fatty acid component. A pharmaceutical compositions may be composed of varying amounts of a fatty acid composition. In certain embodiments, a fatty acid composition constitutes about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein, of the pharmaceutical composition (v/v). In certain embodiments, the pharmaceutical composition consists essentially of the fatty acid composition.

In further embodiments, pharmaceutical compositions and fatty acid compositions include purified fatty acids. A purified fatty acid may be about or at least about 90, 91, 92, 93, 94, 95, 96, 97, 98, 99, 99.1, 99.2, 99.3, 99.4, 99.5, 99.6, 99.7, 99.8, 99.9, or 100% pure, or any range derivable therein. It may or may not be purified from a biological source, such as a plant or animal cell (including human).

It is further contemplated that fatty acids may be synthesized, as opposed to isolated and/or purified from a biological source. Synthesized fatty acids may be subsequently isolated or purified. Fatty acids may be isolated from non-fatty acids. In some embodiments, fatty acids may be purified from non-fatty acids, or a specific fatty acid or combination of fatty acids may be purified from other fatty acids. Compositions may contain fatty acids that have been purified.

In some embodiments, a pharmaceutical or fatty acid composition may include a carrier compound. A fatty acid may be attached or conjugated to the carrier compound. In some embodiments, the carrier compound is attached to one or more fatty acids. In particular embodiments, the carrier compound is conjugated to one or more fatty acids. Alternatively, a carrier compound may be mixed or complexed with one or more fatty acids. In particular cases, a fatty acid is included in a particle that includes or is a carrier compound. In some embodiments, the carrier compound is albumin. In certain cases, it is bovine serum albumin (BSA). In some embodiments, one or more fatty acids is formulated in a lipid vesicle.

It is contemplated that a subject could be a subject in need of physiological hypertrophy, a subject at risk for a cardiovascular disease or condition (a disease of condition that involves the heart and/or blood vessels such as arteries or veins), or a subject exhibiting one or more symptoms of a cardiovascular disease or condition, or a subject diagnosed with a cardiovascular disease or condition. In specific embodiments, the subject is a human patient. Examples of a cardiovascular disease or condition include the following: aneurysm, angina, atherosclerosis, cerebrovascular accident (or stroke), cerebrovascular disease, congestive heart failure, coronary artery disease, myocardial infarction (heart attack), and peripheral vascular disease. In some embodiments, the subject has symptoms of hypertension. Moreover, in certain embodiments, the subject has symptoms or markers indicative of cardiac fibrosis. Methods may also involve determining whether the patient has symptoms or markers indicative of cardiac fibrosis. Methods may also include monitoring the patient for symptoms or markers of a cardiovascular disease or condition before and/or after administration of an AQP7 inducer, such as a composition comprising MPP fatty acids.

In some embodiments, the AQP7 inducer is a small molecule, fatty acid, polypeptide, or nucleic acid. In particular embodiments, the AQP7 inducer is a nucleic acid. In some cases, the AQP7 inducer is a nucleic acid expression vector that encodes an AQP7 polypeptide, which refers to the full-length polypeptide. In some embodiments, a truncated or partial AQP7 polypeptide is encoded or implemented in embodiments.

In further embodiments, an expression vector encoding an AQP7 inducer is a viral vector. In particular embodiments, the viral vector is an adenovirus, adeno-associated virus, lentivirus, retrovirus, herpesvirus, or vaccinia virus. If an adenovirus is employed, the adenovirus may be serotype 5. In specific embodiments, a virus used in methods of the invention is replication-deficient. In cases involving viruses or viral particles, it is contemplated that about $10^7$ to about $10^{15}$ viral particles of the viral vector are administered to the subject for one or more administrations. In particular instances, the viral vector is formulated with protamine. Alternatively or additionally, the viral vector is formulated with one or more lipids.

In other embodiments, methods involve an AQP7 inducer that is a polypeptide. In further embodiments, the polypeptide is a purified polypeptide comprising at least 20, 30, 40, 50, 60, 70, 80, 90, 100, 110, 120, 130, 140, 150, 160, 170, 180, 190, 200, 210 220, 230, 240, 250, 260, or 269 contiguous amino acids of AQP7 (or any ranger derivable therein) or at least 80% of the amino acid sequence of AQP7. In particular embodiments, human AQP7 is employed.

In particular embodiments, methods involve a cardiac cell. In certain instances, the cardiac cell is a myocyte or cardiomyocyte.

In particular embodiments, methods involve an AQP7 inducer that is formulated in a pharmaceutically acceptable composition. In some methods, the AQP7 inducer is administered to the subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularly, mucosally, intrapericardially, intraumbilically, intraocularally, orally, topically, locally, by inhalation, by injection, by infusion, by continuous infusion, by localized perfusion bathing target cells directly, via a catheter, or via a lavage. In particular embodiments, an AQP7 inducer is coated on a stent or via a stent or provided in conjunction with the placement of a stent. In certain embodiments, a pharmaceutical composition is formulated for oral or intravenous (i.v.) delivery. In specific embodiments, a pharmaceutical composition is formulated for oral delivery. In some cases, the pharmaceutical composition is a table, pill, capsule, or lozenge. In further embodiments, the pharmaceutical composition is formulated for extended or sustained release. In particular embodiments, the composition is enterically coated or it has a shell. In certain embodiments, a composition is formulated with a surfactant. In certain embodiments, the pharmaceutical composition is not formulated for topical use.

In some embodiments, an AQP7 inducer is a small molecule. It is contemplated that some AQP7 inducers that are small molecules bind to an AQP7 promoter or portion of the AQP7 promoter ("an AQP7 transcriptional control region"). The small molecule may bind a discrete and specific binding site in the AQP7 promoter.

In certain embodiments the AQP7 inducer is a fatty acid molecule. A fatty acid molecule refers to a compound that is an aliphatic monocarboxylic acid. It is generally unbranched with multiple carbon atoms, and is either saturated or unsaturated. It can have 4, 5, 6, 7, 8, 9, 10, 11, 12, 13, 14, 15, 16, 17, 18, 19, 20, 21, 22, 23, 24, or more carbon atoms, and any range derivable therein.

In specific embodiments, there are compositions and methods involving a pharmaceutical composition comprising a fatty acid composition. In additional embodiments, the composition comprises one or more of these fatty acids isolated from Burmese python serum: myristic acid, palmitic acid, palmitoleic acid, caprylic acid, lauric acid, tridecanoic acid, pentadecanoic acid, stearic acid, oleic acid, linoleic acid, eicosedienoic acid, eicosatrienoic acid, arachidonic acid, and nervonic acid ("python serum fatty acids"). In specific embodiments, a composition comprising MPP fatty acids also includes one, two, three, four, or five of the other python serum fatty acids such as: caprylic acid, lauric acid, tridecanoic acid, pentadecanoic acid, stearic acid, oleic acid, linoleic acid, eicosedienoic acid, eicosatrienoic acid, arachidonic acid, and/or nervonic acid. In certain embodiments, the fatty acid composition comprises myristic acid, alone or combination with palmitic acid and/or palmitoleic acid, and one, two, three, four, or five other python serum fatty acids. In other embodiments, the fatty acid composition comprises palmitic acid, alone or combination with myristic acid and/or palmitoleic acid, and one, two, three, four, or five other python serum fatty acids. In further embodiments, the fatty acid composition comprises palmitoleic acid, alone or combination with palmitic acid and/or myristic acid, and one, two, three, four, or five other python serum fatty acids.

In specific embodiments, a composition does not contain certain components. In some embodiments, the composition does not contain an active ingredient that is not a fatty acid. In particular embodiments, a composition does not contain a therapeutic agent that is not a fatty acid. In additional embodiments, a composition contains one or more fatty acids, but does not contain an anti-inflammatory agent in addition to the fatty acid(s). In some embodiments, a composition contains fatty acids that are unsaturated. In specific embodiments, there are only unsaturated fatty acids in the compositions. In additional embodiments, a composition contains fatty acids that are saturated. In specific embodiments, there are only saturated fatty acids in the compositions. In some embodiments, a composition does not include an antioxidant. In other embodiments, a composition does not contain pyruvate or pyruvic acid.

In some embodiments, an AQP7 inducer is formulated in a pharmaceutically acceptable composition. It is contemplated that formulations may include more than one different inducer, such as 2 or 3 inducers as a cocktail. Alternatively, the AQP7 inducer may be administered before, after, or with a different therapeutic or preventative substance for a cardiovascular disease or condition. Methods of the invention include, in certain embodiments, prescribing or administering one or more other such substances before, after, or in conjunction with an AQP7 inducer to a patient.

In additional embodiments, there are methods for screening for candidate AQP7 inducers comprising: a) contacting one or more candidate compounds with a test nucleic acid, wherein the test nucleic acid comprises a reporter sequence under the control of an AQP7 transcriptional control region; and, b) evaluating expression of the reporter sequence, wherein an increase in expression of the reporter sequence compared to a control identifies the one or more candidate compounds as a candidate AQP7 inducer. In particular embodiments, methods include a step of comparing expression levels involving different candidate compounds or comparing expression levels of one or more candidate compounds to a control. In some embodiments, the reporter sequence encodes a polypeptide that is fluorescent, colorimetric, or enzymatic. In specific embodiments the reporter sequence encodes luciferase or a fluorescent protein such as green fluorescent protein. It is contemplated that candidate compounds may be small molecules, nucleic acids, peptides, polypeptides, or antibodies. They may be part of library or used in conjunction with high throughput screening.

In certain embodiments, screening is conducted using a recombinant host cell containing the test nucleic acid. The host cell can be a mammalian host cell. In certain embodiments, the host cell is a human cell. In particular embodiments, the host cell is a cardiomyocyte. In some cases, cells used are NRVM cells or C2C12 cells. Assays to determine expression levels are well known to those of skill in the art. For instance, quantitative PCR may be employed.

Other aspects of screening methods include identifying the candidate AQP7 inducer, such as when a pool of different inducers are used in screens. Other steps include producing or manufacturing the candidate AQP7 inducer, testing the candidate AQP7 inducer in an animal model, testing it in clinical trials, and/or administering the candidate AQP7 inducer to a cardiomyocyte at risk for or undergoing hypertrophy. The cardiomyocyte may be in a subject in some embodiments.

A method for preparing a pharmaceutical composition in embodiments discussed herein, comprising isolating myristic acid, palmitic acid, and palmitoleic acid; and, formulating the pharmaceutical composition for oral or intravenuous administration to a subject. In certain embodiments, methods include synthesizing one or more fatty acids. Methods may also include a step of purifying one or more fatty acids.

The terms "inhibiting" and "reducing" or any variation of these terms, when used in the claims and/or the specification includes any measurable decrease or complete inhibition to achieve a desired result. The terms "prevention" and "preventing" refer to the expectation that something can be kept from happening to some extent or that the severity, duration, or extent of the condition or disease can be alleviated or reduced. It is contemplated that the terms "treating" or "preventing" in the context of a condition or disease refers to any reduction or inhibition of the disease or condition. In specific embodiments, the disease or condition is cardiovascular disease or condition. In certain other cases, embodiments pertain to cardiovascular diseases or condition that afflicts a certain cell type, tissue, organ or area of the body. In particular embodiments, the cardiovascular condition or disease is a heart condition or disease, which refers to a disease or condition afflicting the heart. In specific embodiments, the heart condition or disease is hypertension. In some embodiments, subjects who may be considered for AQP7 therapy have high blood pressure or they exhibit markers for fibrosis.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention The invention may be better understood by reference to one or more of these drawings in combination with the detailed description of specific embodiments presented herein.

DESCRIPTION OF ILLUSTRATIVE EMBODIMENTS

Figure 1:
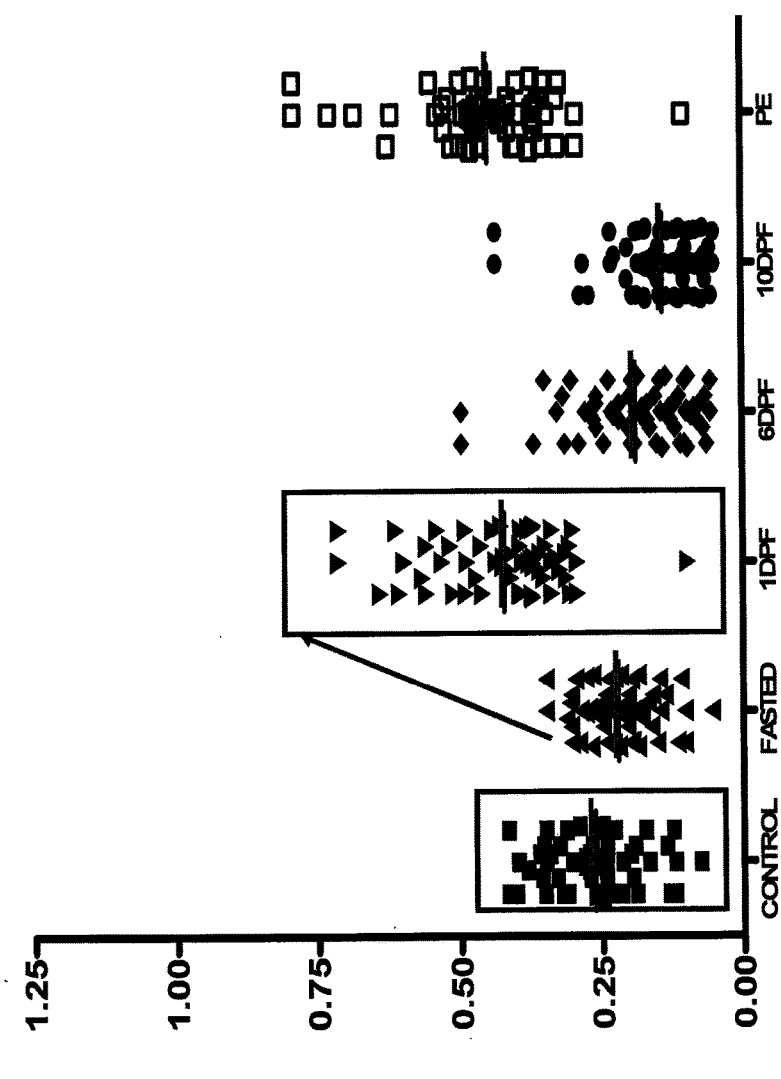
FIG. 1. Serum from fed snakes induces hypertrophy in neonatal cardiomyocytes. Twenty four hours after serum treatment, cardiomyocytes were fixed and immunostained for α-actinin to reveal sarcomere organization and cell morphology. Several images were taken for each condition: fasted (upright black triangles), 1 DPF (head down black triangles), 6 DPF (black rhomboids) and 10 DPF (black circles) and cell size was determined using Image J. Each dot represents the size of a particular cell and at least 50 cells were measured in each condition. Average size is depicted by a horizontal line. As a positive control, cardiomyocytes were treated with 10 μM of phenylephrin (PE; open squares).

All documents, or portions of documents, cited in this application, including but not limited to patents, patent applications, articles, books, and treatises, are hereby expressly incorporated by reference in their entirety.

I. Hypertrophy

Cardiovascular disease remains the number one cause of mortality in the Western world, with heart failure representing the fastest growing subclass over the past 10 years. Heart failure is induced by a number of common disease stimuli, which first activate a phase of cardiac hypertrophy to normalize wall tension in the heart. However, in the long term, myocardial hypertrophy is the biggest predictor of heart failure and sudden death.

The heart responds to a variety of stimuli by an increase in size, also known as "hypertrophy." There are beneficial types of stimuli such as exercise or detrimental ones like when the heart grows in response to high blood pressure, a heart attack or an inherited condition. Defining the differences between the healthy heart growth compared to unhealthy growth is important.

In one aspect, there are compositions and methods useful for treating diseases and conditions related to the activities of cardiac growth or regression related genes or their expressed proteins. These diseases may include, but are not limited to, cachexia, cardiac hypertrophy, high blood pressure, myocardial infarction, cardiac arrhythmia, tachycardia and/or bradycardia. In some embodiments, inhibitors or activators of the identified cardiac growth or regression related genes may be known in the art and any such known inhibitors or activators may be used in the practice of the claimed methods.

The model organisms that are most typically studied to understand cardiac hypertrophy are rodents and humans. Cardiac mass in these organisms can change, but usually slowly and it is rare to see a doubling in heart size without genetic manipulation. Long-term changes in human cardiac mass are not readily amenable to study, as any underlying changes in gene expression or protein activity levels may be difficult to detect. A shorter term model system with greater fluctuations in cardiac mass is desirable, to facilitate detection of genes involved in cardiac hypertrophy or regression.

Burmese pythons (*Python molurus*) are opportunistic ambush predators, adapted to consume large meals at infrequent intervals. As a consequence of their feeding habits, pythons exhibit a large regulatory response to the digestion process including a large increase in its metabolic rate, nutrient transport and organ mass (Secor and Diamond, 1998). Most mammalian species are adapted to consume frequent, small meals, which means that their digestion process does not show a factorial increase like that of pythons.

During fasting conditions, Burmese pythons have a low basal metabolism and most of the organs are maintained with small masses to conserve energy. Upon feeding, the increase in metabolic rate has a peak at 1-2 days and declines to fasting levels at 8-16 days. This rapid increase in energy cost is originated by the rapid start-up of gastrointestinal functions, but also involves the rapid growth of several organs that are not directly involved in digestion, such as the heart.

Increases in oxygen consumption ($VO_2$, 0.76 vs 7.2 ml/Kg min), heart rate (24.7 vs 59.8 beats/min) and systemic blood flow (10.8 vs 42.9 ml/Kg min) illustrate the augmented cardiac output that the heart performs during digestion (Secor et al., 2000). These hemodynamic alterations could lead to cardiac hypertrophy. Indeed, it has been determined that the python heart can enlarge by up to 60% at 2 days post-meal and it reverses to fasting size upon defecation, when digestion is complete. The only molecular investigation on the python published to date showed that the fed python heart increases cardiac myosin RNA by several orders of magnitude (Anderson et al., 2005). The underlying molecular events that trigger the reversible postprandial cardiac growth in pythons have not previously been identified.

Various methods and compositions are disclosed in the Examples section below, relating to detection and/or identification of cardiac growth or regression related genes and/or proteins and/or inhibitors or activators of cardiac growth or regression in the python. The skilled artisan will realize that such genes, proteins, inhibitors or activators may serve as targets for therapeutic intervention in a variety of cardiac-related disease states or conditions or as candidate therapeutic agents for treatment of such disease states or conditions.

A. Aquaporin 7

In some embodiments methods and compositions concern aquaporin (AQP) molecules, which are proteins in the cell membrane that control the flow of water. There are different aquaporin proteins in this family of molecules that transport water in and out of a cell. At least 13 different aquaporin proteins have been identified in mammals, numbered one through 13. The different mammalian aquaporins have their own tissue and cell distribution patterns and they have different and specific functions relative to their location. For instance, AQP1 has been identified in erythrocytes, kidney, lung, eye, choroid plexus, biliary tract, nonfenestrated endothelia, as well as in proximal tubules and descending thin limb of Henle's loop segments. AQP2 has been identified in collecting duct epithelia of kidney. A deficiency of AQP2 can lead to nephrogenic diabetes insipidus, which is characterized by the inability to concentrate urine. AQP3 is located in renal collecting ducts, the gastrointestinal tract, airway epithelia, corneal epithelium and brain. AQP4 is abundant in glial cells and ependymal cell of brain tissue, as well as in retina and airway epithelia. AQP5 can be found in salivary gland; lacrimal gland and lung. AQP6 has been identified in proximal tubular epithelia and collecting duct epithelia of kidney and characteristically acts as intracellular water channel and also is involved in regulation of acid base balance. AQP7 and AQP8 are expressed in germ cells and sperm. AQP9 is abundant in adipocytes (Deen et al., 1999; King et al., 2000; Agre, 2000).

Some embodiments concern specifically aquaporin 7 (AQP7), which is needed for the efflux of glycerol from adipocytes and has been reported to influence glucose levels. In a study of women with severe obesity, investigators determined that AQP7 expression is down-regulated. Ceperuelo-Mallafre et al., 2007, which is hereby incorporated by reference. The human AQP7 nucleic acid coding and protein sequences are located at NM_001170, which is hereby specifically incorporated by reference. Another scientific paper describes AQP7-deficient mice. In Hara-Chikuma et al. (2005), the authors report that older AQP7 null mice showed significant adipocyte hypertrophy and increased body fat. They contemplate that increasing AQP7 expression/function in adipocytes as a way to reduce adipocyte volume and fat mass in obesity.

Aquaporin family members have been mentioned or described in a number of different patent applications and/or patents. In U.S. Pat. No. 6,506,377, which is specifically incorporated by reference, is entitled "Interferon-alpha mediated upregulation of aquaporin expression." It concerns applications for improving pulmonary function by administering interferon compounds to lung cells. It is contemplated that compounds discussed in the patent may be implemented in methods described and/or claimed herein.

U.S. Pat. No. 7,192,951, which is hereby incorporated by reference, discusses the action of vasopressin antagonists on AQP2 in kidneys for use at a treatment of cardiac edema. Such vasopressin antagonists may be implemented in methods described and/or claimed herein.

In U.S. Patent Publication 20070203083, which is hereby incorporated by reference, methods for reducing metabolic rates are discussed in this publication. Such methods involve an agent that decreases the expression or activity of Gapba or a gene that has a Gapba binding site. AQP7 is identified as having a Gapba binding site. Any agents disclosed in the patent publication may be implemented in methods described and/or claimed herein.

U.S. Patent Publication 20050186290, which is hereby incorporated by reference, describes the use of aquaglyceroporin modulators as slimming agents by reducing the volume of adipocytes. Such modulators may be implemented in methods described and/or claimed herein.

Other publications describe treating a patient suffering from a disease or condition mediated by an aquaporin or by abnormal expression of an aquaporin. In U.S. Patent Publication 20080221169, which is specifically incorporated by reference, compounds are described as potential modulators of aquaporin expression. It is contemplated that such modulators may be implemented in methods described and/or claimed herein.

U.S. Patent Publication 20070009474, which is hereby incorporated by reference, describes aquaporin stimulating agents that can be used to regulate the condition of mammalian keratinous tissue. It is contemplated that such agents may be implemented in methods described and/or claimed herein.

B. Fatty Acids

Embodiments concern fatty acid compositions. Fatty acids that may be employed include, but are not necessarily limited to, the following saturated and unsaturated fatty acids: myristic acid, palmitic acid, palmitoleic acid, caprylic acid, lauric acid, tridecanoic acid, pentadecanoic acid, stearic acid, oleic acid, linoleic acid, eicosedienoic acid, eicosatrienoic acid, arachidonic acid, and nervonic acid. In certain embodiments, a composition may specifically not contain one or more of these listed fatty acids. For example, a composition may exclude eicosedienoic acid, or any of the other fatty acids in the list.

Myristic acid, also known as tetradecanoic acid, n-Tetradecanoic acid, or C14:0, is a saturated fatty acid. Palmitic acid, also known as hexadecanoid acid or C16:0, is the commonest saturated fatty acid in plant and animal lipids. Palmitoleic acid, also known as (z)-9-hexadecenoic acid or C, 16.1 is an omega-7 monounsaturated fatty acid that is a common component of glucerides in human adipose tissue. It is made from palmitic acid using the enzyme delta-9 desaturase. Other fatty acids include, but are not limited to, those found in python serum such as caprylic acid (C8:0), lauric acid (C12:0), tridecanoic acid (C13:0), pentadecanoic acid (C15:0), stearic acid (C18:0), oleic acid (C18:1n9), linoleic acid (C:18:2), eicosedienoic acid (C20:2), eicosatrienoic acid (C20:3), arachidonic acid (C:20:4), and nervonic acid (C20:4).

Compositions and methods include any of these fatty acids singly or solely, or they may be used in a combination of fatty acids. In some embodiments, a combination includes or is limited myristic and palmitoleic acids. In other embodiments, a combination includes or is limited myristic and palmitic acids. In additional embodiments, a combination includes or is limited palmitic and palmitoleic acids. In particular embodiments, a combination includes at least myristic, palmitic, and or palmitoleic acids. In certain embodiments, a composition may specifically not contain one or more python serum fatty acids.

C. Polynucleotides and Nucleic Acids

Some embodiments concern polynucleotides or nucleic acid molecules relating to an aquaporin 7 sequence in diagnostic, therapeutic, and preventative applications. In certain embodiments, aquaporin 7 is involved in the prevention or treatment of a cardiovascular condition or disease. Nucleic acids or polynucleotides of the invention may be DNA or RNA, and they may be olignonucleotides (100 residues or fewer) in certain embodiments. Moreover, they may be recombinantly produced or synthetically produced.

These polynucleotides or nucleic acid molecules may be isolatable and purifiable from cells or they may be synthetically produced. In some embodiments of the invention, an AQP7-encoding nucleic acid is employed.

As used in this application, the term "polynucleotide" refers to a nucleic acid molecule, RNA or DNA, that has been isolated free of total genomic nucleic acid. Therefore, a "polynucleotide encoding AQP7" refers to a nucleic acid sequence (RNA or DNA) that contains AQP7 coding sequences, yet may be isolated away from, or purified and free of, total genomic DNA and proteins.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 2001; Ausubel, 1996). There may be times when the full or partial genomic sequence is some. Alternatively, cDNAs may be advantageous because it represents coding regions of a polypeptide and eliminates introns and other regulatory regions. In certain embodiments, nucleic acids are complementary or identical to cDNA encoding sequences, such as a AQP7 upstream sequence, a NM_001170 sequence (human), a NM_019157 sequence (rat), or a NM_007473.4 sequence (mouse). Embodiments are specifically contemplated to include the use of all or part of these sequences or their gene products.

The term "gene" is used for simplicity to refer to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule hybridizing to NM_001170, NM_019157, or NM_007473.4 may comprise a contiguous nucleic acid sequence of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more (or any range derivable therein) nucleotides, nucleosides, or base pairs of the NM_001170, NM_019157, or NM_007473.4 sequences. Such sequences may be identical or complementary to SEQ ID NO:1 (cDNA for NM_00170), SEQ ID NO:3 (cDNA for NM_019157), SEQ ID NO:5 (cDNA for NM_007473.4), SEQ ID NO:21, or any other sequences disclosed herein.

Accordingly, sequences that have or have at least or at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% and any range derivable therein, of nucleic acids that are identical or complementary to a nucleic acid sequence of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 contiguous bases (or any range derivable therein) of SEQ ID NO:1 (human AQP7) or any other AQP7 are contemplated as embodiments. They may be used in methods concerning the prevention or treatment of cardiovascular diseases or conditions or in the induction of hypertrophy.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

1. Vectors

Vectors of the present invention are designed primarily to introduce into cells a therapeutic or preventative AQP7 nucleic acid inducer under the control of a eukaryotic promoter (i.e., constitutive, inducible, repressible, tissue specific). Also, the vectors may contain a selectable marker if, for no other reason, to facilitate their manipulation in vitro. However, selectable markers may play an important role in producing recombinant cells. In certain embodiments, the AQP7 coding sequence is provided as a nucleic acid expressing the AQP7 polypeptide. In specific embodiments, the nucleic acid is a viral vector, wherein the viral vector dose is or is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles. In certain embodiments, the viral vector is an adenoviral vector, a retroviral vector, a vaccinia viral vector, an adeno-associated viral vector, a polyoma viral vector, an alphaviral vector, a rhabdoviral vector, or a herpesviral vector. Most preferably, the viral vector is an adenoviral vector. In other specific embodiments, the nucleic acid is a non-viral vector.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term "promoter" will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

In some embodiments, the promoter for use in the present invention is the cytomegalovirus (CMV) immediate early (IE) promoter. This promoter is commercially available from Invitrogen in the vector pcDNAIII, which is some for use in the present invention. Other viral promoters, cellular promoters/enhancers and inducible promoters/enhancers may be used in combination with the present invention. Additionally any promoter/enhancer combination (as per the Eukaryotic Promoter Data Base EPDB) could also be used to drive expression of a nucleic acid of interest.

Another signal that may prove useful is a polyadenylation signal. Such signals may be obtained from the human growth hormone (hGH) gene, the bovine growth hormone (BGH) gene, or SV40.

The use of internal ribosome binding sites (IRES) elements are used to create multigene, or polycistronic, messages. IRES elements are able to bypass the ribosome scanning model of 5-methylatd cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs of the present invention are functionally positioned downstream of a promoter element.

Compositions and methods of the invention are provided for administering the compositions of the invention to a patient.

Any nucleic acid molecule of the invention may be comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1996, both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

One method for delivery of the recombinant DNA involves the use of an adenovirus expression vector. "Adenovirus expression vector" is meant to include those constructs containing adenovirus sequences sufficient to (a) support packaging of the construct and (b) to ultimately express a recombinant gene construct that has been cloned therein. The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

The retroviruses are a group of single-stranded RNA viruses characterized by an ability to convert their RNA to double-stranded DNA in infected cells by a process of reverse-transcription (Coffin, 1990). In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors include adeno-associated virus (AAV) (described in U.S. Pat. No. 5,139,941 and U.S. Pat. No. 4,797,368, each incorporated herein by reference), retroviruses, vaccinia virus, other poxviruses, lentivirus, Epstein Barr viruses, and picornaviruses.

2. Antisense Sequences, Including siRNAs

Particular embodiments concern isolated nucleic acid segments and recombinant vectors incorporating DNA sequences that encode AQP7 inducers, such as siRNAs or ribozymes that target nucleic acids encoding inhibitors of AQP7, such as AQP7 transcription repressors.

In some embodiments, a nucleic acid may encode an antisense construct. Antisense methodology takes advantage of the fact that nucleic acids tend to pair with "complementary sequences." By complementary, it is meant that polynucleotides are those which are capable of base-pairing according to the standard Watson-Crick complementarity rules. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

In certain embodiments, the nucleic acid encodes an interfering RNA or siRNA. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp and Zamore, 2000; Tabara et al., 1999). Activation of these mechanisms targets mature, dsRNA-complementary mRNA for destruction. Advantages of RNAi include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, C. elegans, Trypanasoma, Drosophila, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

In some embodiments, methods concern an siRNA that is capable of triggering RNA interference, a process by which a particular RNA sequence is destroyed. siRNA are dsRNA molecules that are 100 bases or fewer in length (or have 100 basepairs or fewer in its complementarity region). In some cases, it has a 2 nucleotide 3' overhang and a 5' phosphate. The particular RNA sequence is targeted as a result of the complementarity between the dsRNA and the particular RNA sequence. It will be understood that dsRNA or siRNA of the invention can effect at least a 20, 30, 40, 50, 60, 70, 80, 90 percent or more reduction of expression of a targeted RNA in a cell. dsRNA of the invention (the term "dsRNA" will be understood to include "siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, to sequences (or their complements) disclosed herein.

3. Aptamers

In certain embodiments, an inhibitor, activator or binding agent of use may be an aptamer. Aptamers are usually single-stranded, short molecules of RNA, DNA or a nucleic acid analog, that may adopt three-dimensional conformations complementary to a wide variety of target molecules. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the target-binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

The aptamers used as starting materials in the process to determine specific binding sequences may be single-stranded or double-stranded DNA or RNA. In a preferred embodiment, the sequences are single-stranded DNA, which is less susceptible to nuclease degradation than RNA. In preferred embodiments, the starting aptamer will contain a randomized sequence portion, generally including from about 10 to 400 nucleotides, more preferably 20 to 100 nucleotides. The randomized sequence is flanked by primer sequences that permit the amplification of aptamers found to bind to the target. For synthesis of the randomized regions, mixtures of nucleotides at the positions where randomization is desired may be added during synthesis.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) are retained during separation. Each cycle results in an enrichment of aptamers with high affinity for the target. Repetition for between three to six selection and amplification cycles may be used to generate aptamers that bind with high affinity and specificity to the target. Aptamers may be selected to bind to and inhibit or activate one or more proteins products of cardiac growth or regression related genes.

4. Protamine Delivery of Nucleic Acids

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference.

5. Lipid Formulations for Nucleic Acid Delivery

In a further embodiment of the invention, a nucleic acid may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Advances in lipid formulations have improved the efficiency of gene transfer in vivo (Smyth-Templeton et al., 1997; WO 98/07408). A novel lipid formulation composed of an equimolar ratio of 1,2-bis(oleoyloxy)-3-(trimethylammonio)propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

In further embodiments, the liposome is further defined as a nanoparticle. A "nanoparticle" is defined herein to refer to a submicron particle. The submicron particle can be of any size. For example, the nanoparticle may have a diameter of from about 0.1, 1, 10, 100, 300, 500, 700, 1000 nanometers or greater. The nanoparticles that are administered to a subject may be of more than one size.

Any method known to those of ordinary skill in the art can be used to produce nanoparticles. In some embodiments, the nanoparticles are extruded during the production process. Information pertaining to the production of nanoparticles can be found in U.S. Patent App. Pub. No. 20050143336, U.S. Patent App. Pub. No. 20030223938, U.S. Patent App. Pub. No. 20030147966, each of which is herein specifically incorporated by reference into this section.

In certain embodiments, an anti-inflammatory agent is administered with the lipid to prevent or reduce inflammation secondary to administration of a lipid:nucleic acid complex. For example, the anti-inflammatory agent may be a non-steroidal anti-inflammatory agent, a salicylate, an anti-rheumatic agent, a steroid, or an immunosuppressive agent.

Synthesis of DOTAP:Chol nanoparticles is by any method known to those of ordinary skill in the art. For example, the method can be in accordance with that set forth in Chada et al., 2003, or Templeton et al., 1997, both of which are herein specifically incorporated by reference. DOTAP:Chol-DNA complexes were prepared fresh two to three hours prior to injection in mice.

One of ordinary skill in the art would be familiar with use of liposomes or lipid formulation to entrap nucleic acid sequences. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Liu et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

The liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

A nucleic acid for nonviral delivery may be purified on polyacrylamide gels, cesium chloride centrifugation gradients, column chromatography or by any other means known to one of ordinary skill in the art (see for example, Sambrook et al., 2001, incorporated herein by reference). In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, bulk of cellular components or in vitro reaction components, and/or the bulk of the total genomic and transcribed nucleic acids of one or more cells. Methods for isolating nucleic acids (e.g., equilibrium density centrifugation, electrophoretic separation, column chromatography) are well known to those of skill in the art.

D. Proteins and Polypeptides

The present invention is directed to methods and compositions involving an AQP7 inducer that is a polypeptide. In some methods an AQP7 inducer is an AQP7 peptide or polypeptide. In certain embodiments, methods involve AQP7 peptides or polypeptides in the treatment or prevention of cardiovascular conditions or diseases. The terms "protein" and "polypeptide" are used interchangeably herein and they both cover what is understood as a "peptide" (a polypeptide molecule having 100 or fewer amino acid residues). In certain embodiments, the AQP7 inducer is a protein, polypeptide, or peptide; in particular embodiments, the AQP7 inducer is protein or polypeptide that is an antibody. In some cases, the antibody binds to an AQP7 inhibitor, that is, a molecule that inhibits AQP7 expression, stability or activity.

Peptides and polypeptides may be based on SEQ ID NO:2 (human protein from NM_00170), SEQ ID NO:4 (rat protein from NM_019157) or SEQ ID NO:6 (mouse protein from NM_007473.4).

As will be understood by those of skill in the art, modification and changes may be made in the structure of an AQP7 polypeptide or peptide or AQP7 inducer, and still produce a molecule having like or otherwise desirable characteristics. For example, certain amino acids may be substituted for other amino acids or include deletions, additions, or truncations in the protein sequence without appreciable loss of interactive binding capacity with structures. Since it is the interactive capacity and nature of a protein that defines that protein's biological functional activity, certain amino acid sequence substitutions can be made in a protein sequence (or, of course, its underlying DNA coding sequence) and nevertheless obtain a protein with similar inhibitory properties. It is thus contemplated by the inventors that various changes may be made in the sequence of AQP7 inducer polypeptides or peptides (or underlying DNA) without appreciable loss of their biological utility or activity.

It is also well understood that where certain residues are shown to be particularly important to the biological or structural properties of a protein or peptide, e.g., residues in the binding site of an antibody, such residues may not generally be exchanged.

Amino acid substitutions are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all a similar size; and that phenylalanine, tryptophan, and tyrosine all have a generally similar shape. Therefore, based upon these considerations, the following subsets are defined herein as biologically functional equivalents: arginine, lysine, and histidine; alanine, glycine, and serine; and phenylalanine, tryptophan, and tyrosine.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, some, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2, ±1, or ±0.5 is contemplated.

While discussion has focused on functionally equivalent polypeptides arising from amino acid changes, it will be appreciated that these changes may be effected by alteration of the encoding DNA, taking into consideration also that the genetic code is degenerate and that two or more codons may encode the same amino acid.

1. In Vitro Protein Production

In addition to the purification methods provided in the examples, general procedures for in vitro protein production are discussed. Following transduction with a viral vector according to some embodiments of the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshney, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present invention uses autologous B lymphocyte cell lines, which are transfected with a viral vector that expresses an immunogene product, and more specifically, a protein having immunogenic activity. Other examples of mammalian host cell lines include Vero and HeLa cells, other B- and T-cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

E. Small Molecules

Embodiments concern AQP7 inducers that are small molecules, which refers to a small compound that is biologically active but is not a polymer. It does refer to a monomer. In certain embodiments, the small molecule is capable of inducing AQP7 expression or activity. In some embodiments it is contemplated that the small molecule induces AQP7 transcription. In certain embodiments the small molecule interacts with the AQP7 promoter or other transcription controlling region to allow for more AQP7 transcription. In certain embodiments, F. Screening Methods Putative AQP7 inducers may be may be tested for the ability to increase AQP7 expression and/or activity. For example, compositions may be tested for an ability to increase AQP7 transcripts or protein or for increased AQP7 activity. In some embodiments this is achieved by evaluating transcript or protein levels of AQP7 or by measuring transcription activity from an AQP7 transcription region controlling expression of a marker gene. For instance, transcription from an endogenous AQP7 gene can be measured or evaluated or transcription can be measured from a recombinant and/or exogenous AQP7 coding sequence under the control of an AQP7 promoter and/or enhancer region. Transcription levels can be measured by a number of assays that are well know to those of skill in the art.

In other embodiments inducers may be screened based on protein or activity levels. These may be of AQP7 itself or of proteins in an AQP7-dependent pathway. Protein levels may be evaluated by a number of assays well known to those of skill in the art including flow cytometric assay, affinity column chromatography, solid-phase binding assay or any binding assays known in the art. The ability of putative inducers to affect expression of AQP7 genes may be determined by known assays, as described in more detail below. For example, model cell lines or intact organs or tissues may be assayed for the levels of expressed proteins in the presence or absence of putativeinducers using antibodies against one or more AQP7 protein products. Alternatively, AQP7 activity is known and assays to evaluate that activity are employed. For instance, assays may involve assessing or evaluating the amount of water inside and/or outside a cell. Assays may also involve qualititative assessments of activity.

For convenience, a putative AQP7 inducer may be referred to below as a test substance(s). A test substance may be or include a nucleic acid, polypeptide, or small molecule. Several types of in vitro assays may be performed using an AQP7 sequence. In some embodiments purified or semi-purified AQP7 protein can be used In one such assay, purified protein or a fragment thereof may be immobilized by attachment to the bottom of the wells of a microtiter plate. The test molecule(s) can then be added either one at a time or simultaneously to the wells. After incubation, the wells can be washed and assayed to determine the degree of protein binding to the test molecule. Binding may be determined by a multiplicity of known techniques, for example by "tagging" the test molecule(s) with a detectable radioactive, fluorescent, luminescent or other label. In variations of such assays, the test molecule(s) may be attached to the solid substrate and purified or semi-purified protein product added. Binding of protein to the substrate may be monitored, for example, using labeled primary or secondary antibodies against the protein of interest. Typically, the molecule will be tested over a range of concentrations, and a series of control wells lacking one or more elements of the test assays are used to detect non-specific binding.

According to preferred embodiments, one may expose a cell line, such as neonatal rat cardimyocytes (NRVMs) to test substances to determine whether the cell line exhibits AQP7 activity, such as hypertrophy. In some embodiments, the test substances may comprise python serum or purified or partially purified components thereof, collected at different stages in the post-prandial cardiac growth and regression cycle. Serum may be subjected to various treatments, such as heat inactivation, protease, lipase or nuclease treatment, or may be fractionated using any known techniques for molecular and/or complex separation. These are well known in the art and may include filtration, centrifugation, solvent extraction, HPLC, FPLC, gel permeation chromatography, ion exchange chromatography, affinity chromatography, reverse-phase chromatography, phase separation, gel electrophoresis under non-denaturing conditions and similar known techniques.

1. Regulation of Endogenous Gene Expression

In certain embodiments, an AQP7 inducer may act by increasing transcription of a gene, such as AQP7. Such assays may be conducted in vivo or in vitro. They need not involve the entire AQP7 gene and may contain only a region that regulates AQP7 transcription. For instance, a reporter gene may be used to measure the level of expression from a transcriptional regulatory region(s) that controls AQP7 transcription. In some embodiments, a transcriptional regulatory region includes all or part of SEQ ID NO:21 or a sequence in another organism that corresponds to SEQ ID NO:21. SEQ ID NO:21 is the upstream sequence from the rat AQP7 gene. The assay may involve a single transcription binding site, multiple sites, or all or part of the AQP7 promoter region. In some embodiments, the AQP7 regulatory region may involve a PPARγ agonist binding site. Duan et al. (2005), which is hereby incorporated by reference, reports that agonists for perixosome proliferator-activated receptor (PPAR)-γ, specifically the thiazolidinedione rosiglitazone, cause cardiac hypertrophy.

In some embodiments, assays are conducted in a cell-free system, while in others, tissue culture cells are employed. It is contemplated that highthroughput screening assays may be employed to identify AQP7 inducers. In specific embodiments, a reporter gene assay will be used in conjunction with highthroughput screening. It is specifically contemplated that such screening may involve a variety of small molecule candidates, such as can be found in a library. Certain embodiments include methods for screening for candidate AQP7 inducers comprising: a) contacting a candidate AQP7 compound with a nucleic acid molecule comprising a reporter gene under the control of a cardiocyte AQP7 control region, where the AQP7 control region is all or part of a nucleic acid sequence that controls the transcriptional regulation of the AQP7 gene in cardiocytes and b) assaying for expression of the reporter gene. A candidate AQP7 compound that induces expression of the reporter gene relative to one or more controls is a candidate AQP7 inducer. Controls include but are not limited to a parallel assay conducted with the nucleic acid molecule in the absence of the candidate AQP7 compound or involving the same candidate compound but with a different nucleic acid molecule, such as one under the control of a different transcriptional regulation region. It is contemplated that methods may be conducted partly or fully in a cell-free system, though in other embodiments, the nucleic acid molecule is in a host cell. In some embodiments, the host cell is a cardiomyocyte. It is specifically contemplated that nucleic acid molecules, control regions, and/or host cells may be of human origin or other mammalian origin.

In particular embodiments, nucleic acids may be analyzed to determine levels of expression, particularly using nucleic acid amplification methods. Nucleic acid sequences (mRNA and/or cDNA) to be used as a template for amplification may be isolated from cells contained in a biological sample, according to standard methodologies. The nucleic acid may be fractionated or whole cell RNA. Where RNA is used, it may be desired to convert the RNA to a complementary cDNA. In one embodiment, the RNA is whole cell RNA and is used directly as the template for amplification.

In one example, the determination of expression is performed by amplifying (e.g. by PCR) the mRNA or cDNA sequences and detecting and/or quantifying an amplification product by any methods known in the art, including but not limited to TaqMan assay (Applied Biosystems, Foster City, Calif.), agarose or polyacrylamide gel electrophoresis and ethidium bromide staining, hybridization to a microarray comprising a specific probe, Northern blotting, dot-blotting, slot-blotting, etc.

Various forms of amplification are well known in the art and any such known method may be used. Generally, amplification involves the use of one or more primers that hybridize selectively or specifically to a target nucleic acid sequence to be amplified. One of the best-known amplification methods is the polymerase chain reaction (referred to as PCR) which is described in detail in U.S. Pat. Nos. 4,683,195, 4,683,202 and 4,800,159.

One embodiment of the invention may comprise obtaining a suitable sample from an individual and detecting a messenger RNA. Once the tissue sample is obtained the sample may be prepared for isolation of the nucleic acids by standard techniques (e.g., cell isolation, digestion of membranes, Oligo dT isolation of mRNA etc.) The isolation of the mRNA may also be performed using kits known to the art (Pierce, AP Biotech, etc). A reverse transcriptase PCR amplification procedure may be performed in order to quantify an amount of mRNA amplified. Methods of reverse transcribing RNA into cDNA are well known and described in Sambrook et al., 1989. Alternative methods for reverse transcription utilize thermostable DNA polymerases.

2. Purification of Active Molecules or Complexes

In certain embodiments, one or more candidate molecules may be isolated or purified. Molecular purification techniques are well known to those of skill in the art. The molecule(s) of interest may be purified using chromatographic and electrophoretic techniques to achieve partial or complete purification (or purification to homogeneity). Analytical methods particularly suited to molecular purification are ion-exchange chromatography, gel exclusion chromatography, HPLC, FPLC, polyacrylamide gel electrophoresis, affinity chromatography, immunoaffinity chromatography and isoelectric focusing. An example of purification by affinity chromatography is disclosed in U.S. Pat. No. 5,206,347.

Other purification techniques known in the art include, for example, precipitation with ammonium sulfate, PEG, antibodies and the like, or by heat denaturation, followed by centrifugation or filtration; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the molecule(s) of interest always be provided in their most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of molecule or comlpex, or in maintaining the activity of a regulatory molecule.

Affinity chromatography is a chromatographic procedure that relies on the specific affinity between a substance to be isolated and a molecule to which it can specifically bind to. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

G. Pharmaceutical Compositions

In some embodiments, one or more inhibitors or activators may be administered to a subject with a disease. Such agents may be administered in the form of pharmaceutical compositions. Generally, this will entail preparing compositions that are essentially free of impurities that could be harmful to humans or animals.

One generally will employ appropriate salts and buffers to render therapeutic agents stable and allow for uptake by target cells. Aqueous compositions may comprise an effective amount of an inhibitor or activator, dissolved or dispersed in a pharmaceutically acceptable carrier or aqueous medium. The phrase "pharmaceutically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

The pharmaceutical forms suitable for use include sterile aqueous solutions or dispersions and sterile powders for the preparation of sterile solutions or dispersions. It must be stable under the conditions of manufacture and storage and must be preserved against the contaminating action of microorganisms, such as bacteria and fungi.

In certain embodiments, an effective amount of a therapeutic agent must be administered to the subject. An "effective amount" is the amount of the agent that produces a desired effect. An effective amount will depend, for example, on the efficacy of the agent and on the intended effect. An effective amount of a particular agent for a specific purpose can be determined using methods well known to those in the art.

1. Pharmaceutically Acceptable Carriers

As used herein, "pharmaceutically acceptable carrier" includes any and all solvents, dispersion media, coatings, antibacterial and antifungal agents, isotonic and absorption delaying agents, and the like that are physiologically compatible. In particular embodiments, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the presence of microorganisms may be ensured both by sterilization procedures and by the inclusion of various antibacterial and antifungal agents, for example, paraben, chlorobutanol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

A "pharmaceutically acceptable salt" refers to a salt that retains the desired biological activity of the parent compound and does not impart any undesired toxicological effects (see e.g., Berge et al., 1977). Examples of such salts include acid addition salts and base addition salts.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific antibody.

2. Therapeutically Effective Dosages

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the therapeutic agent is being used, the route of administration, and the size (body weight, body surface or organ size) and condition (the age and general health) of the patient. Accordingly, the clinician may titer the dosage and modify the route of administration to obtain the optimal therapeutic effect.

A therapeutically effective amount is typically an amount such that when administered in a physiologically tolerable composition is sufficient to achieve a plasma of, for example, from about 0.01 µg/ml to about 300 µg/ml. In another embodiment, the concentration may be from about 1 µg/ml to about 300 µg/ml. In yet another embodiment, the concentration may be from about 1 µg/ml to about 75 µg/ml. In yet another embodiment, the concentration may be from about 15 µg/ml to about 50 µg/ml. Dosages may, of course, vary according to frequency and duration of administration.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

A physician or veterinarian having ordinary skill in the art can readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved. In general, a suitable daily dose of a composition will be that amount of the compound which is the lowest dose effective to produce a therapeutic effect.

3. Routes of Administration

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a catheter, membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some embodiments, a pharmaceutical composition is administered via a catheter delivery system. In certain cases the delivery is to the left ventricle. Examples include, but are not limited to, U.S. Pat. No. 6,669,716, ALLIANCE™ Catheter Delivery System, ATTAINT™ Catheter delivery system, U.S. Pat. No. 5,891,084, WO Published Application 2005/120626, US patent publication 20080264102, and US Patent publication 20050197694, all of which are hereby incorporated by reference. In other embodiments a side port needle is employed.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al. (1983)], poly (2-hydroxyethyl-methacrylate) [Langer et al. (1981)] and [Langer et al. (1982)], ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al. (1985); EP 36,676; EP 88,046; EP 143,949.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

4. Peptide Administration

Various embodiments of the claimed methods and/or compositions may concern one or more therapeutic peptides to be administered to a subject. Administration may occur by any route known in the art. In certain embodiments, oral administration is contemplated.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are known (see, for example, Blondelle et al., 1995; Ecker and Crooke, 1995; Goodman and Ro, 1995; Goodman and Shao, 1996). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct therapeutic peptides suitable for oral administration to a subject.

In certain embodiments, preparation and administration of peptide mimetics that mimic the structure of any selected peptide may be used within the scope of the claimed methods and compositions. In such compounds, the standard peptide bond linkage may be replaced by one or more alternative linking groups, such as $CH_2-NH$, $CH_2-S$, $CH_2-CH_2$, $CH=CH$, $CO-CH_2$, $CHOH-CH_2$ and the like. Methods for preparing peptide mimetics are well known (for example, Hruby, 1982; Holladay et al., 1983; Jennings-White et al., 1982; Almquiest et al., 1980; Hudson et al., 1979; Spatola et al., 1986; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, therapeutic peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709). The skilled artisan will be aware that peptide modification should be followed by testing for target binding activity to direct the course of peptide modification. In certain embodiments, peptides and/or proteins may be orally administered by co-formulation with proteinase- and/or peptidase-inhibitors.

H. Kits

Various embodiments may concern kits containing components suitable for treating or diagnosing diseased tissue in a patient, such as AQP7 inducers.

The kit components may be packaged together or separated into two or more separate containers. In some embodiments, the containers may be vials that contain sterile, lyophilized formulations of a composition that are suitable for reconstitution. A kit may also contain one or more buffers suitable for recosititution and/or dilution of other reagents. Kit components may be packaged and maintained sterilely within the containers. Another component that can be included is instructions for use of the kit.

EXAMPLES

The following examples are included to demonstrate preferred embodiments of the invention. It should be appreciated by those of skill in the art that the techniques disclosed in the examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Animals

Burmese pythons were purchased commercially (Captive Bred Reptiles) and they were maintained individually in 20 l plastic boxes at 27-29° C. under a 14 L:10 D photoperiod. For several months prior to the study, snakes were feed biweekly with a diet of rodents with water available ad libitum. Juvenile Burmese pythons with body masses ranging from 600 g-700 g were fasted for 30 days. To induce the post-prandial response they were fed rodent meals equivalent to 25% of the snake's body mass. At each time point (0, 0.25, 0.5, 1, 2, 3, 4, 6, 10, and 15 days post feeding) 2 snakes were sacrificed and serum was collected.

Masson trichrome-stained sections were made of a fasted and a fed snake after 3 days of a rodent meal. The increase in size of hearts among similar size snakes was observed. Collagen staining was employed and no obvious differences between the two conditions were observed.

Blood from a fasted and 1 day post-fed snake was drawn and serum was obtained by centrifugation after allowing the serum to clot. Fasted serum is clear in contrast to the 1 day post-fed sample, which has a high content of triglycerides and lipids.

Antibodies

α-actinin (A5044) antibody was purchased from Sigma-Aldrich. Alexa Fluor 488 (A21202) anti-mouse was purchased from Molecular Probes, Invitrogen.

DNA and Adenovirus Constructs

Aquaporin 7 (Aqp7) rat cDNA, gi 27734167, was obtained by PCR from neonatal rat cardiomyocytes total cDNA using the following primers:

```
                                         (SEQ ID NO: 7)
Fw 5' CGCG AGATCT ACCATGGCCGGTTCTGTGCT 3'

(SEQ ID NO: 8)
Rv 5' GGCC TCTAGA CTAAGAACCCTGTGGTGGTATGC 3'
```

The PCR product was cloned directly into the multiple cloning site of the pShuttle-CMV vector using Bgl II and XbaI restriction sites and confirmed by sequencing. The Aqp7 recombinant adenovirus was generated by using the full-length rat Aqp7 into the pShuttle with the AdEasy Adenoviral Vector System according to the manufacturer's instructions (Qbiogene, Inc).

Cell Culture and Adenoviral Infection

Primary culture cardiomyocytes prepared from neonatal rats were treated with fasted and post-fed serum samples. Twenty four hours later the cells were removed from the culturing dish and analyzed for changes in cell size by immunostaining or by automatic analyzer such as Coulter Counter.

In other experiments, neonatal rat cardiac myocytes (NRVMs) were prepared according to the method described in Waspe et al. (1990). In brief, cells were obtained from the hearts of Sprague-Dawley rat pups (1-2 days old) by trypsinization and plated in MEM medium (Hanks' salts) with 5% calf serum. After 48 h in culture, cells were transferred to serum-free medium supplemented with transferring and insulin (each 10 μg/ml). Cells were maintained in 60- or 35-mm culture dishes at a density of 200,000 cells/ml. Contaminating non-muscle cells were kept at <10% by pre-plating and addition of 0.1 mM bromodeoxyuridine to the medium though day 3 of culture.

Cells were transduced with an adenovirus expressing Aqp7 or with a control adenovirus at a multiplicity of infection of 20 plaque-forming units/cell. 48 h after, cells were fixed and stained for analysis. The stained cells were analyzed and images from representative fields were acquired. Sarcomeres were observed.

Serum Extraction and Cardiac Myocyte Treatment

Blood samples were obtained from euthanized pythons in sterile glass tubes at different time points after feeding. The samples were incubated at 37° C. for 30 min to allow clotting and centrifuged at 1500 rpm for 10 min. Serum was stored in 500 μl aliquots and snap frozen to preserve the quality of the samples. For longer storage serum samples were kept at −80° C.

Before treating the cells, serum samples were thawed and heat inactivated at 58° C. for 30 min. On day 2 of culture python heat inactivated serum was added to the dishes at 2% final concentration unless specified. Cells were harvested at 48 h after additions for cell size measurements and RNA isolation.

α-Actinin Staining and Cell Size Measurements

Cardiomyocytes grown on gelatin-coated coverslips were infected with Ad_Aqp7 for 48 h. Immunofluorescence was performed according to Harrison et al. (2004). Cells were washed with Tris-buffered saline/Tween 20 (TBST) and fixed with 4% paraformaldehyde for 15 min. Cells were again washed with TBST and incubated with 0.1% Triton X for 30 min. Cells were then blocked with 2% horse serum in TBST for 1 h followed by 1 h incubation each with 1:200 dilution of α-actinin antibody and 1:500 Alexa fluor 488 secondary antibody. Images were captured at a 40× magnification with a fluorescence microscope (Nikon E800) equipped with a digital camera (AxioCam) and Axiovision, version 3.0.6.36 imaging software (Carl Zeiss, Thornwood, N.Y.). The surface areas were measured using NIH image software (Image J) and at least 100 individualized cells were analyzed per each experiment. Cell size was also determined by particle size analyzer, Coulter Counter Multisizer 3 (Beckman Dickinson).

Cardiac Myocyte Transfection

Cardiac myocyte transfections were performed using the nucleofaction protocol (Amaxa Biosystems, Gaithersburg, Md.). This methodology results in approximately 50% transfection efficiency. Briefly, $2 \times 10^6$ cells were transfected with 4 µg of plasmid DNA according to the manufacturer's recommendations.

Gene Expression Profiling and Microarray Data Analysis

Total RNA was purified with RNeasy Micro Kit MinElute Spin Columns (Qiagen) and eluted into 14 µl of RNase-free. The quality of the RNA is essential to the overall success of gene expression analysis using microarray technology; thus stringent quality checks were carried out at all stages. The concentration and purity of the total RNA samples were first assessed by spectrophotometry (Qubit, Invitrogen). Samples were further analyzed for quantity and integrity using the Agilent Bioanalyzer (Agilent Technologies). Samples that met the quality control criteria were used as templates for cRNA synthesis and biotin labeling, incorporating a single round of linear amplification, using the GeneChip Expression 3'-Amplification One-cycle cDNA synthesis kit followed by IVT labeling reaction (Affimetrix, Inc). Samples were subsequently prepared for hybridization using the Affymetrix hybridization control kit (Affymetrix, Inc). All samples were hybridized to Rat Genome 230 plus 2.0 GeneChip arrays for 16 h. Following hybridization, the GeneChip arrays were stained and washed and fluorescent signals were detected using the Affymetrix GeneChip Scanner 3000 (Affymetrix, Inc), which provides an image of the array and automatically stores high-resolution fluorescence intensity data. These data were initially documented using Affymetrix Microarray Suite software which generates an expression report file that lists the quality control parameters. All of these parameters were scrutinized to ensure that array data had reached the necessary quality standards. For each time point three different samples were analyzed.

Hierarchical Clustering for Changes in Gene Expression Upon Serum Treatment

Neonatal rat cardiomyocytes were untreated (C) or treated with fasted (F), 3 DPF (P) and phenylephrin (P) for 48 hours. Each condition was assayed in triplicates. RNA was extracted and the samples were analyzed for changes in gene expression by microarray using rat gene chips from Affymetrix. The gene chip results were normalized and analyzed by hierarchical clustering, were statistical analysis group similar changes in gene expression within a same group by connecting them with brackets.

Real-Time Polymerase Chain Reaction (PCR)

Total RNA was extracted by TRIzol (Invitrogen). 0.5 µg of RNA was reverse transcribed into cDNA using the SuperScript III first-strand cDNA synthesis kit (Invitrogen). Typically, 0.1 ng of cDNA, 12.5 nM of each primer, and Power SYBER Green PCR Master Mix (Applied Biosystems, Foster City, Calif.) were used in the reverse transcription (RT)-PCR reactions. Reactions were performed using the ABI7300 system. The primers used are presented on Table 1.

TABLE 1

| Primer Sequence for Rat Genes | |
|---|---|
| αMyHC F | CCTGTCCAGCAGAAAGAGC (SEQ ID NO: 9) |
| αMyHC R | CAGGCAAAGTCAAGCATTCATATTTATTGTG (SEQ ID NO: 10) |
| BNP F | GGTGCTGCCCCAGATGATT (SEQ ID NO: 11) |
| BNP R | CTGGAGACTGGCTAGGACTTC (SEQ ID NO: 12) |
| SERCA F | GGCCAGATCGCGCTACA (SEQ ID NO: 13) |
| SERCA R | GGGCCAATTAGAGAGCAGGTTT (SEQ ID NO: 14) |
| Sk α-actin F | CCACCTACAACAGCATCATGAAGT (SEQ ID NO: 15) |
| Sk α-actin R | GACATGACGTTGTTGGCGTACA (SEQ ID NO: 16) |
| βMyHC F | CGCTCAGTCATGGCGGAT (SEQ ID NO: 17) |
| βMyHC R | GCCCCAAATGCAGCCAT (SEQ ID NO: 18) |
| ANF F | GCGAAGGTCAAGCTGCTT (SEQ ID NO: 19) |
| ANF R | CTGGGCTCCAATCCTGTCAAT (SEQ ID NO: 20) |

Pre-designed TaqMan assays (Applied Biosystems, Foster City, Calif.) were used to determine gene expression of candidate genes to validate microarray analysis. The results were detected on an ABI PRISM 7900 Sequence Detection System (Applied Biosystems).

Example 2

Experiments with Burmese Pythons

The enlargement of the heart is known as cardiac hypertrophy and there are two types: physiologic and pathologic hypertrophy. Physiologic hypertrophy is beneficial for the heart function and does not correlate with heart disease; however, the pathologic growth is detrimental for the heart and progress to cardiac dilation and heart failure.

Burmese pythons (*Python molurus*) are opportunistic ambush predators, adapted to consume large meals at infrequent intervals. As a consequence of their feeding habits, pythons exhibit a large regulatory response to the digestion process including a large increase in its metabolic rate, nutrient transport and organ mass including the heart. Understanding the cellular and molecular components of this rapid and reversible enlargement of the heart provides a better understanding of the mechanisms that regulate cardiac growth under physiological conditions in mammals.

We have conducted experiments to gain insights into the remodeling process that occurs during the response of the snake heart to feeding. Histological analyses of the hearts dissected in both experimental conditions have been performed. In accordance with a physiological hypertrophy, Masson's trichrome staining showed no increased collagen deposition in the hypertrophied heart.

Figure 2:
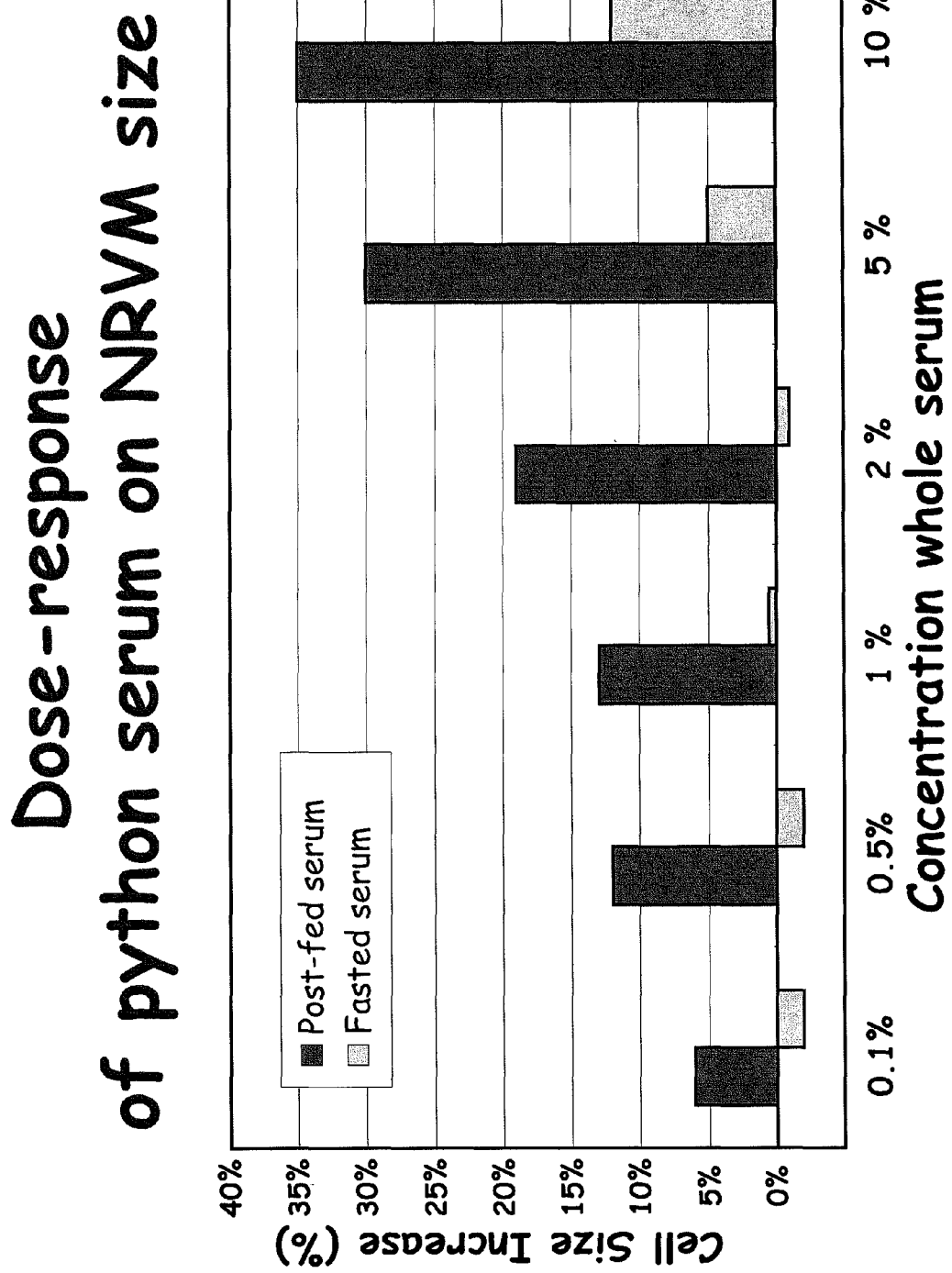
FIG. 2. Dose-response of python serum effect on NRVM size. Neonatal rat cardiomyocytes were treated with increasing concentrations of python serum. 48 hours later, cells were trypsinized and resuspended in PBS/1% calf serum to be analyzed in a particle size analyzer *Coulter Counter, Beckman). Mean cell volume was obtained and the percentage of cell size change was calculated by comparing each condition to untreated cells. Light gray and dark gray bars represent the effect of increasing concentrations of fasted and 3 day post-fed serum respectively.

We have been able to show that snake serum contains a pro-hypertrophic factor by treating neonatal ventricular myocytes with 2% fed snake serum and measuring changes in cell size. Serum from a fed snake one day after a rodent meal (1 DPF) induced a significant increase in cardiomyocyte size compared to a fasted one. Indeed, the magnitude of the cell growth is comparable to a well-know pro-hypertrophic agonist such as phenylephrin (PE) (FIG. 1). We have also determined that there is a dose-dependent response to the molecule present in the serum (FIG. 2).

Figure 3:
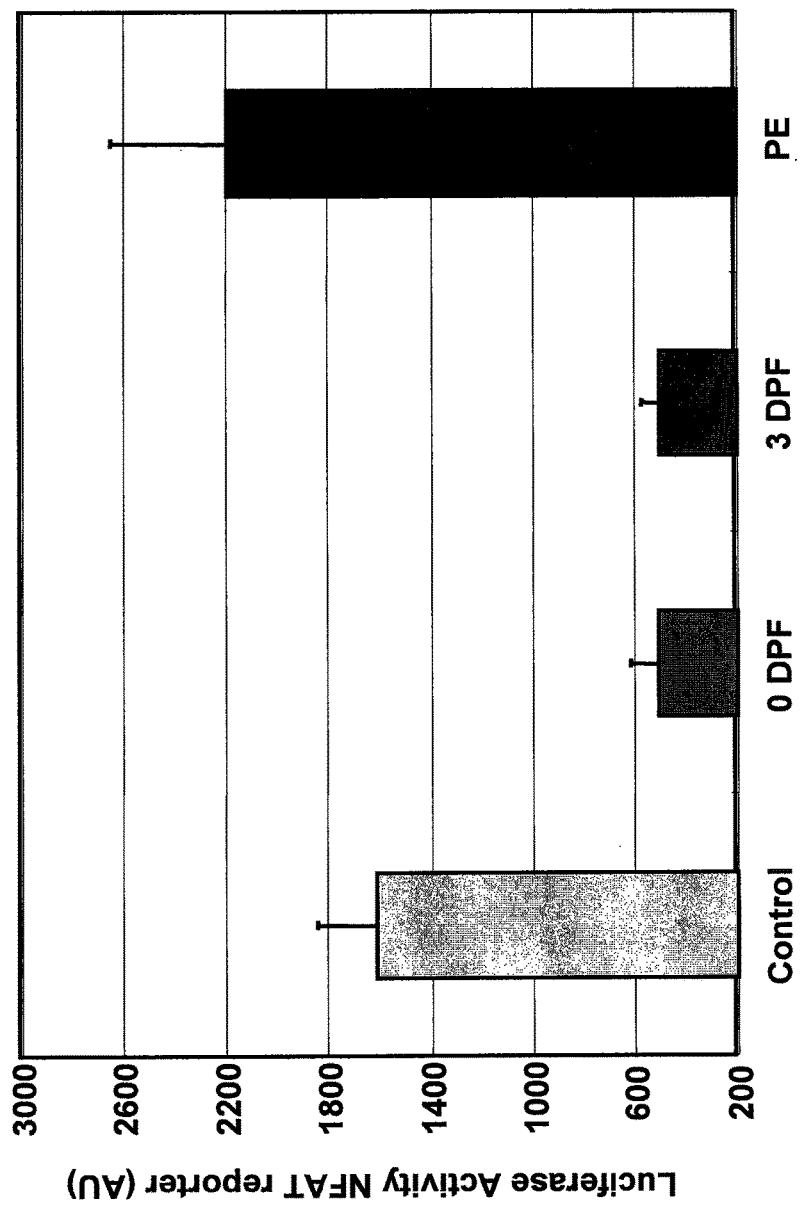
FIG. 3. Fed serum induces cardiomyocytes growth in a NFAT independent manner. Neonatal rat cardiomyocytes were transduced with an adenoviral vector containing 4 tandem repeats for NFAT binding site along with the cDNA for luciferase. 24 hours later, the cells were untreated (Control; white bar) or treated with 0 DPF (medium gray bar), 3 DPF (dark gray bar) and PE (black bar). Cells were lysed 24 hours later and luciferase activity was measured in the lysates. Each condition was analyzed in triplicate and the average and standard deviation were plotted.

A key feature of the cardiomyocytes growth is the increase in protein synthesis. mTOR and the IGF signaling pathway are good candidate molecules that may be induced by snake serum. In fact, when we determined the activation of NFAT upon fed serum treatment there is a repression of this transcription factor which is an event downstream the proteins activated by calcium and that correlated with pathologic hypertrophy (FIG. 3).

Figure 4:
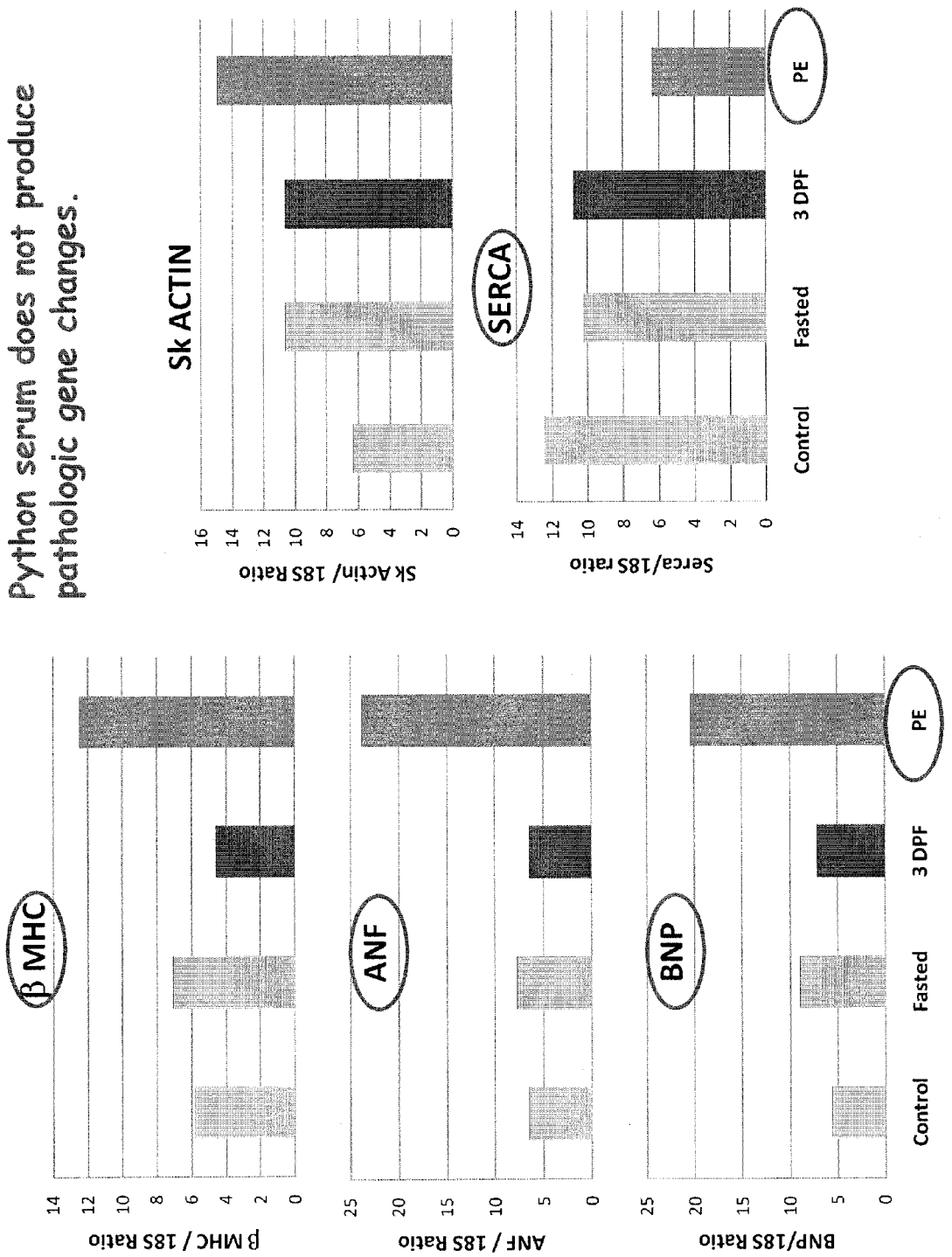
FIG. 4. Hypertrophic growth induced by fed serum does not correlate with the expression of pathologic fetal genes. Neonatal rat cardiomyocytes were untreated (lightest gray bars) or treated with fasted serum (light gray bars), post-fed serum (black bars) and Phenylephrin (PE; dark gray bars). After 48 hours, RNA was isolated and cDNA was obtained by standard procedures. The expression of several pathologic hypertrophic markers was measured by quantitative real-time PCR including β-myosin heavy chain, atrial natriuretic factor (ANF), brain natriuretic peptide (BNP), skeletal actin and sarcoplasmic reticulum calcium ATPase (SERCA).

Another important aspect of this characterization was to determine whether the snake serum induces or not the reactivation of fetal genes which is a hallmark of the pathologic cardiac growth. By qPCR, we demonstrated that the serum does not induce the activation of the fetal gene program which is another evidence to support the idea of the python model as a physiologic type of heart hypertrophy (FIG. 4).

Figure 5:
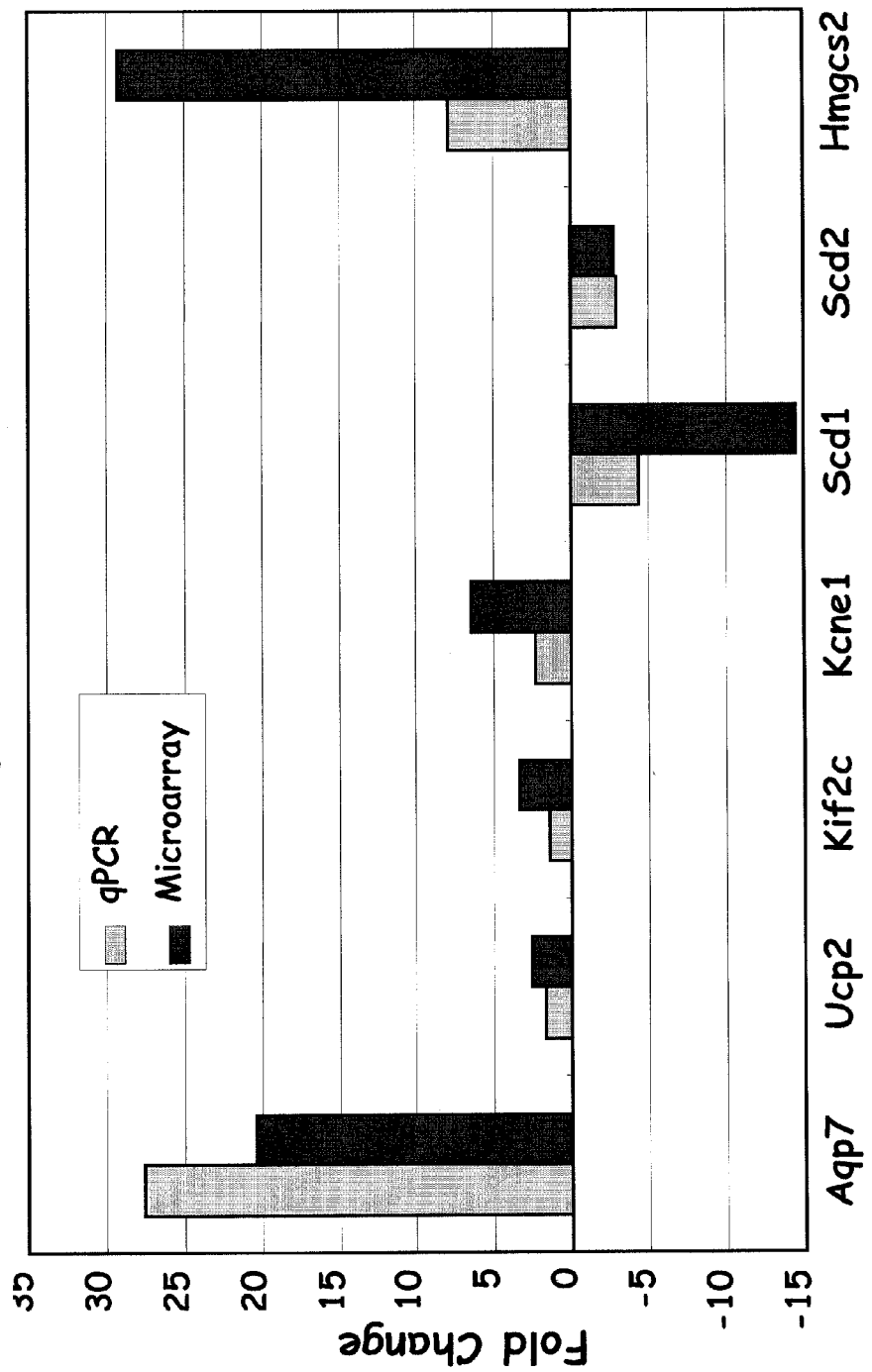
FIG. 5. Changes in gene expression were validated by quantitative Real Time PCR. RNA samples obtained for microarray analysis were subjected to gene analysis by qPCR (light gray bars). cDNA was synthesized and specific TaqMan probes were purchased. Candidate genes representing the group of up-regulated and down-regulated genes were chosen and the results for changes in gene expression were graphed. qPCR results are illustrated in light blue and compared to microarray results (dark gray).

In an effort to understand the primary cause of cardiac enlargement we performed microarray analysis on neonatal cardiac myocytes treated for 48 hours with python serum (fasted and fed). At this time the cells show a moderate increase in size; however our hypothesis is that genes responsible for cell growth have been already activated. Moreover, we included in this analysis primary cardiac cells treated with phenylephrin (PE) which is a well established stimuli that induces pathologic cardiac hypertrophy. Comparing physiologic to pathologic cardiac growth signaling pathways will allow us to narrow down the search for beneficial molecules in the python serum. In order to group and classify the data, hierarchical clustering was performed after normalization and statistical analysis. The analysis shows that the replicates group together. A set of unique genes that were significantly regulated by serum treatment were identified. These include the following up-regulated genes: Myosin LC1, Aquaporin 7, Calponin 1, Hsp70, and Na Channel (VG). Down-regulated genes included the following: dehydrogenase/reductase, cdk inhibitor, and Ca++ ATPase. It was important to validate our array analysis and to do so, the differential expression of some candidate genes up- and down-regulated was determined by qPCR (FIG. 5).

Figure 6:
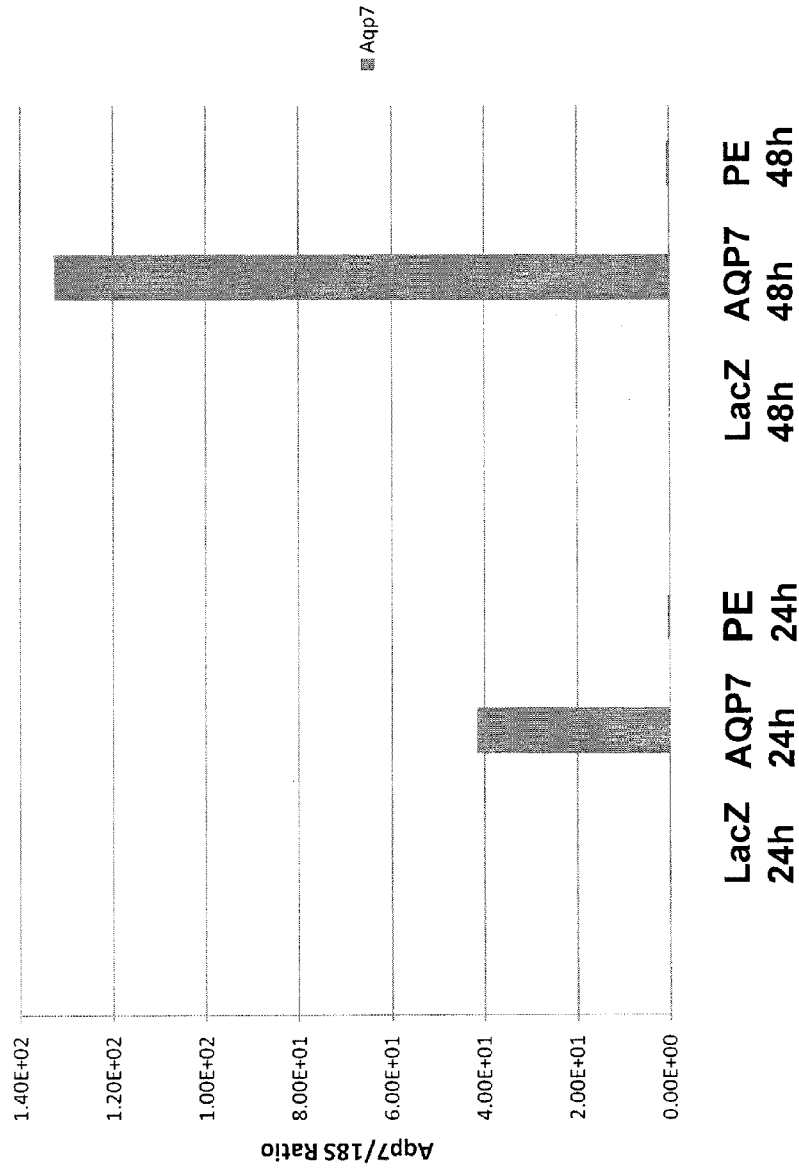
FIG. 6. An adenovirus encoding AQP7 was used to infect NRVMs. AQP7 mRNA is overexpressed in NVRMs infected with the adenoviral vector.
Figure 7:
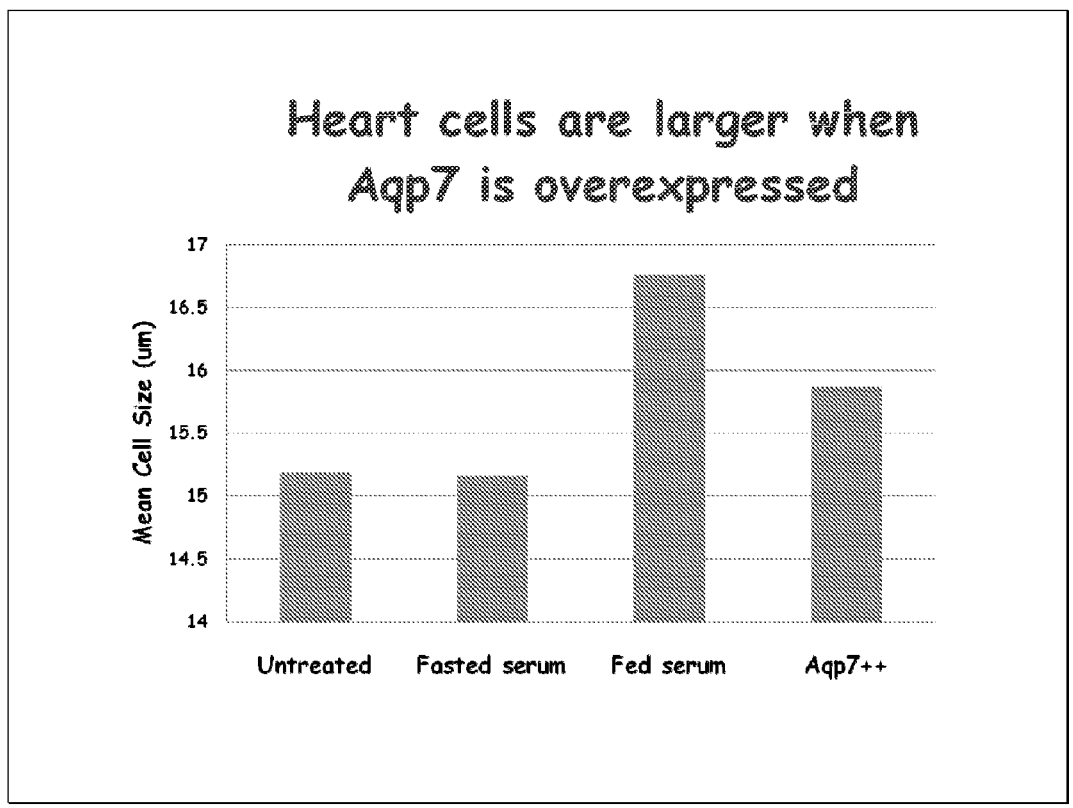
FIG. 7. Heart cells are larger when AQP7 is overexpressed.

Aquaporin 7 (AQP7) belongs to a family of water-selective membrane channels. Specifically, AQP7 facilitates water, glycerol and urea transport. There is evidence that AQP7 is expressed in the mammalian heart but its function and the relevance for the heart function are subjects to be determined. Based on the array analysis performed on the cardiomyocytes where AQP7 is 60-fold up-regulated upon fed serum, we believe that this protein could be an important molecule for the regulation of physiologic cardiac growth. In order to further pursue AQP7 function, we cloned the rat sequence in an adenoviral vector. The AQP7-containing adenoviral constructs were transduced in NVRMs and AQP7 mRNA was overexpressed in NVRMs infected with the AQP7-adenoviral vector (FIG. 6). The induction of cardiac cell growth was visualized by alpha actinin staining (and DAPI for nuclei). Compared to the untransduced cells, the AQP7 cardiomyocytes were evidently bigger. Cell size was also measured to confirm that treated cells were bigger. (FIG. 7). These results indicate that the overexpression of AQP7 induced a signaling event that mimics a prohypertrophic factor.

Example 3

Characterization of Serum

Materials and Methods

Inhibition of Fatty Acid Transport Blocks Serum-Induced NRVM Hypertrophy.

Synthesis of Sulfo-N-succinimidyl oleate (SSO) was performed as described by Harmon et al. (*J. Membr Biol.*; 121:261-268; 1991), which is hereby incorporated by reference. Briefly, oleate (0.25 mM), HOSu($SO_3$)Na (0.25 mM), and dicyclohexylcarbodiimide (DCC) (0.275 mM) were dissolved in 0.5 ml of dry N,N-dimethylformamide (DMF) and stirred overnight at room temperature. Precipitated dicyclohexyturea was removed by filtration, and the filtrate cooled to 3° C. for 4 hours. Eight volumes of ethyl acetate were added, and the precipitated product was collected by filtration under nitrogen and then stored in a vacuumed desiccator over phosphorus pentoxide. Neonatal rat ventricular myocytes (NRVMs) were cultured in serum-free media (MEM/Hepes/PB12) containing insulin, transferrin, BSA, and BrdU. NRVMs were treated with serum (2%) in the presence and absence of SSO (400 µM) for 48 hours and cell size was determined using a Coulter Counter.

Analysis of Python Plasma Fatty Acid Composition by Gas Chromatography.

125 µl of python serum was heated in 1 ml methanol (2.5% $H_2SO_4$) at 80° C. for 1 hour and then cooled to room temperature. 450 µl of hexane was added and the samples were mixed and centrifuged. The upper phase (fatty acyl methyl esters) was then transferred to a new tube, 100 µl of FAME was added, and gas chromatography was performed on an Agilent HP6890N platform equipped with a DB-23 column (30 m×250 µm×0.25 µm).

Fasted Plasma Supplemented with C16, C16:1, and C14 Recapitulates the Fed Plasma Effect.

Individual fatty acids were complexed to BSA as described by de Vries et al. (*J. Lipid Res.*; 38:1384-1394; 1997), which is hereby incorporated by reference. Briefly, C16, C16:1, and C14 were dissolved in ethanol to yield a concentration of 18.75 mM. An equal volume of $Na_2CO_3$ (10 mM) was added and the ethanol was evaporated at 60° C. under continuous $N_2$ flow. The fatty acid mix was added dropwise to 10% BSA. BSA/fatty acid complexes were then dialyzed four times at 4° C. during 4-6 hours in $NH_4HCO_3$ (0.1 M). Complexes were then frozen, lyophilized overnight, and resuspended in NRVM rinse media (MEM/PB12/Hepes) for a final concentration of 7 mM. NRVMs were treated with fasted serum, 1 day post-fed serum, or fasted serum+individual fatty acids. Serum was added for a final concentration of 2%; individual fatty acids were supplemented to 1 day post-fed levels (C14, 40 µM; C16, 137 µM; C16:1, 7.5 µM). NRVM gene expression and mean cell diameter were determined after either 24 or 48 hours, respectively.

Results

Inhibition of fatty acid transport blocks hypertrophic effect of python plasma. As discussed above, lipids extracted from whole plasma recapitulate the hypertrophic effect induced in cardiomyocytes in culture supplemented with python plasma. To explore the role of plasma-containing fatty acids (FA) as putative pro-hypertrophic factors, cardiomyocytes were cultured in the absence or presence of sulfo-N-succinimidyl oleate (SSO) to achieve the inhibition of CD36 mediated LCFA transport. The readout of the experiment is changes in cell size determined by Coulter Counter. Although the cardiomyocytes are smaller in the presence of SSO and no serum (control), the inhibitor completely blocks the cell growth induced by the fed-serum (2% 1DPF) indicating that indeed the fatty acids present in the fed serum are key to induce growth in cardiac cells.

Fatty Acid Composition of Python Plasma Throughout Digestion.

Figure 8:
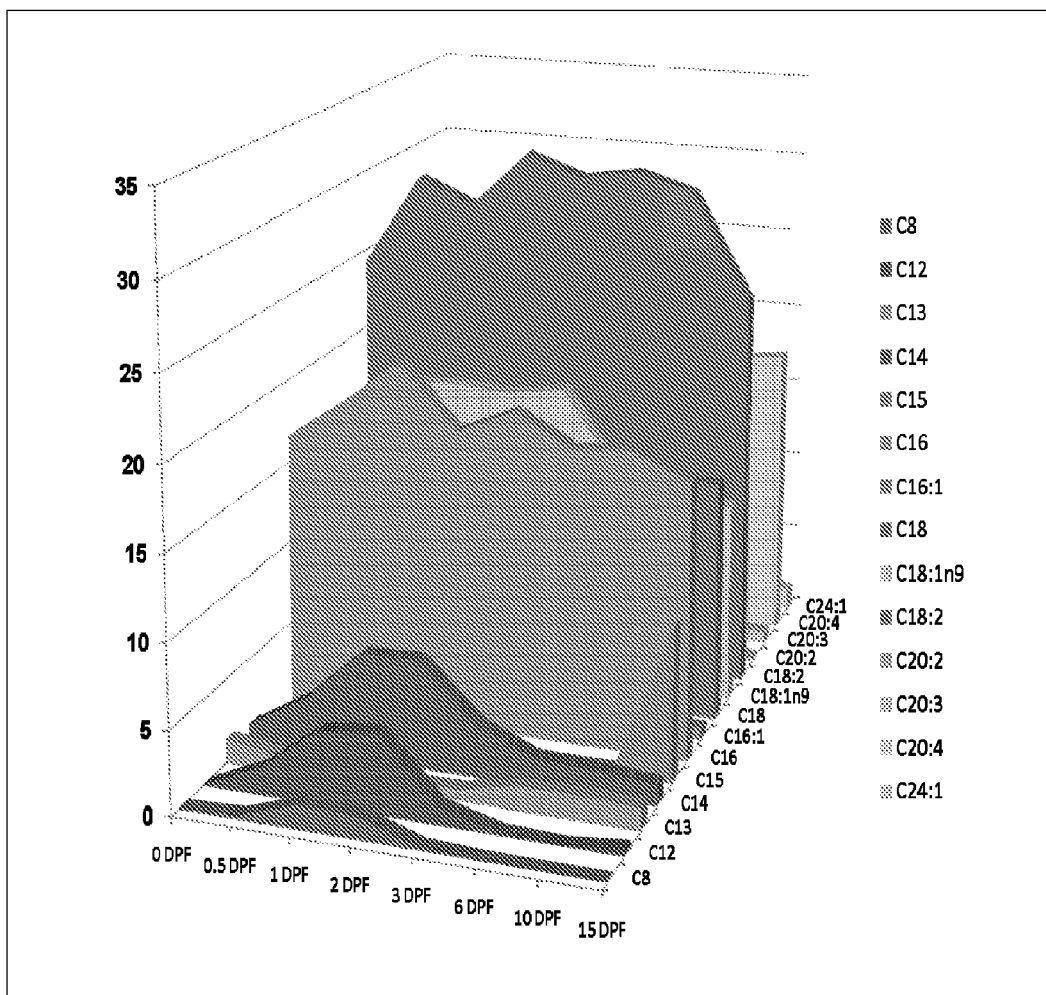
FIG. 8. Fatty acid composition of python plasma throughout digestion. Gas chromatography was used to analyze qualitative and quantitative changes of plasma fatty acid profile throughout digestion.

The previous experiments suggest a direct link between fatty acids present in fed python plasma and the capacity of fed plasma to induce cardiac growth. In order to identify specific fatty acid specie(s) responsible for such an effect, the qualitative and quantitative changes of plasma fatty acid profile throughout digestion were explored. Lipids were extracted from 4 plasma samples at different time points after feeding and analyzed by gas chromatography (FIG. 8). The identification of each fatty acid species was inferred by the retention time exhibited in the analysis compared to a standard curve. The relative concentration of each fatty acid was determined by the quantification of the area of each peak at each time point. The total amount of free fatty acid was determined by the sum of all species detected at each time point and the composition of the python plasma fatty acids is presented here as averaged percentage of each individual FFA from the total amount at a given time point. The graph shows that fed plasma between 1 DPF to 3 DPF had significantly higher total plasma FFAs than did earlier or later fed plasma samples. Among all FFA, C16, C18, C18:1, C18:2, C20:4 were found to be the most abundant ones and the plasma concentration of C16, C18:1 and C18:2 increased between 1-3 DPF, but it was not as significant as other fatty acids. Interestingly, there are less abundant species that had more dramatic changes at the mentioned time points. Among them C12, C14 and C16:1 were the FFA species that stand out, having showed an increase of 4, 6 and 4 times their percentage from total, respectively.

Fatty Acid Species Complexed with BSA.

Figure 9:
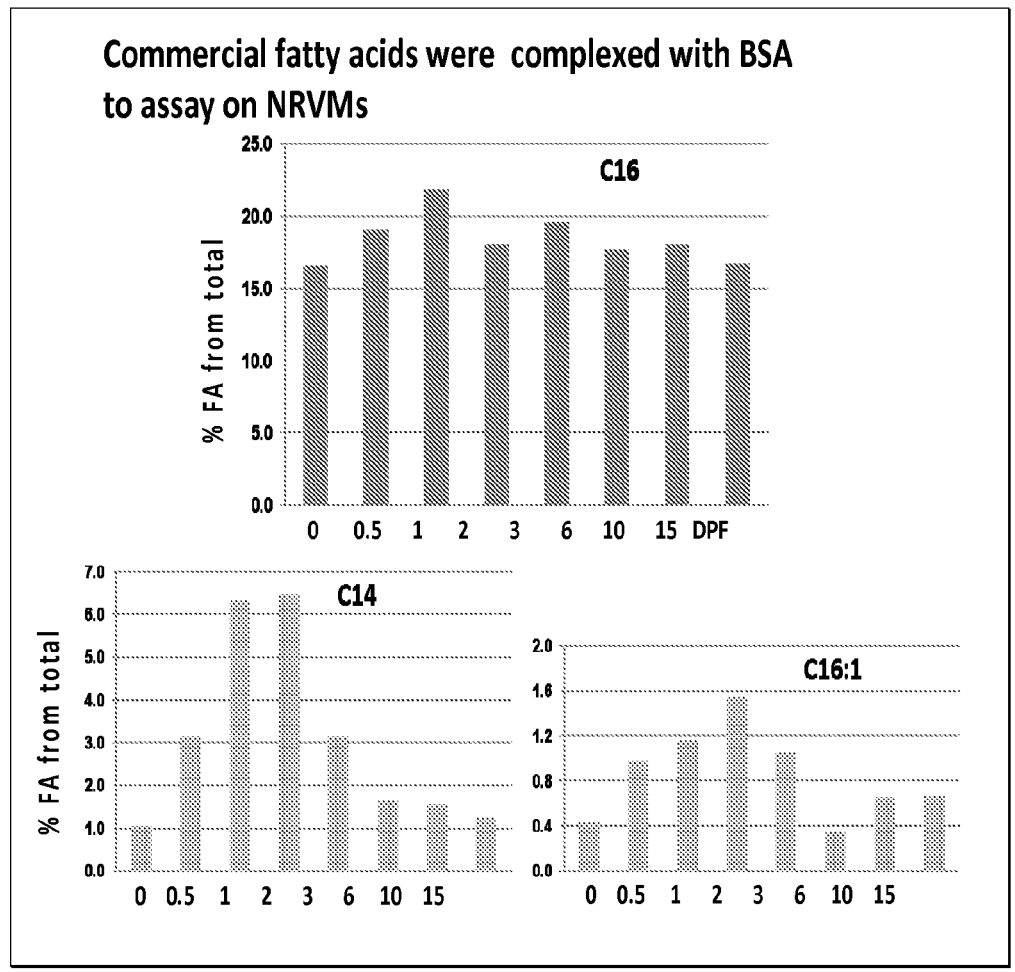
FIG. 9. Fatty acid species complexed with BSA. Fatty acids were added to fasted plasma as a 1 DPF-like plasma.

Now that the unique lipid profiles at each time after feeding were obtained, analysis was conducted to reconstitute a fasted plasma as a 1 DPF-like plasma by adding the appropriate concentration of the FFA that had changed the most. In order to do so, C16, C14 and C16:1 was purchased from Sigma and complexed to albumin (BSA) to ensure their solubility in the cardiomyocytes culture media. C16 was chosen to represent one of the abundant FFAs and C14 and C16:1 as putative hypertrophic molecules. (FIG. 9).

Figure 10:
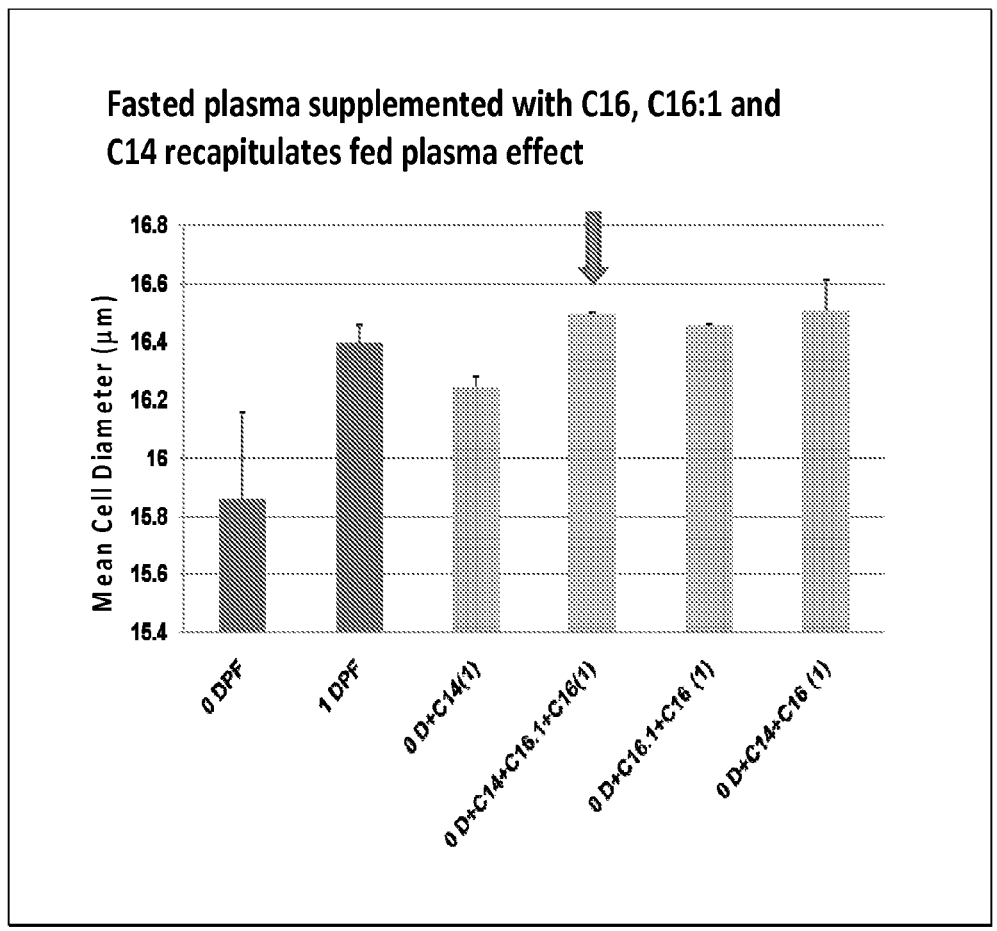
FIG. 10. Fasted plasma supplemented with the appropriate concentration of C16, C14 and C16:1 recapitulates fed plasma affect. Neonatal rat cardiomyocytes were given fasted plasma with particular fatty acids or combinations of fatty acids. Cell size was subsequently evaluated.

Fasted plasma supplemented with the appropriate concentration of C16, C14 and C16:1 recapitulates fed plasma affect. The role of these specific FFAs was examined as potential signaling molecules that regulate cardiac growth. Different mixtures of fasted plasma was generated by supplementing the plasma with each of the FFAs or a combination of them. These were used to treat neonatal rat cardiomyocytes. Changes in cell size were evaluated after 48 hours in the above mentioned conditions (FIG. 10). The two darker gray bars on the left side of the panel demonstrate the response of the cells to fasted (0 DPF) and 1DPF plasma. The lighter gray bars represent the effect of fasted plasma mixed with the indicated FFAs. The addition of C14 at 1DPF-like concentration induced a significant increase in cell size; however the combination of C14 and C16:1 had the most potent effect comparable to the whole 1 DPF plasma. This result confirmed the relevance of myristic and palmitoleic acid in inducing cardiac hypertrophy.

Aquaporin 7 Expression is Highly Induced by Fatty Acid Treatment.

Figure 11:
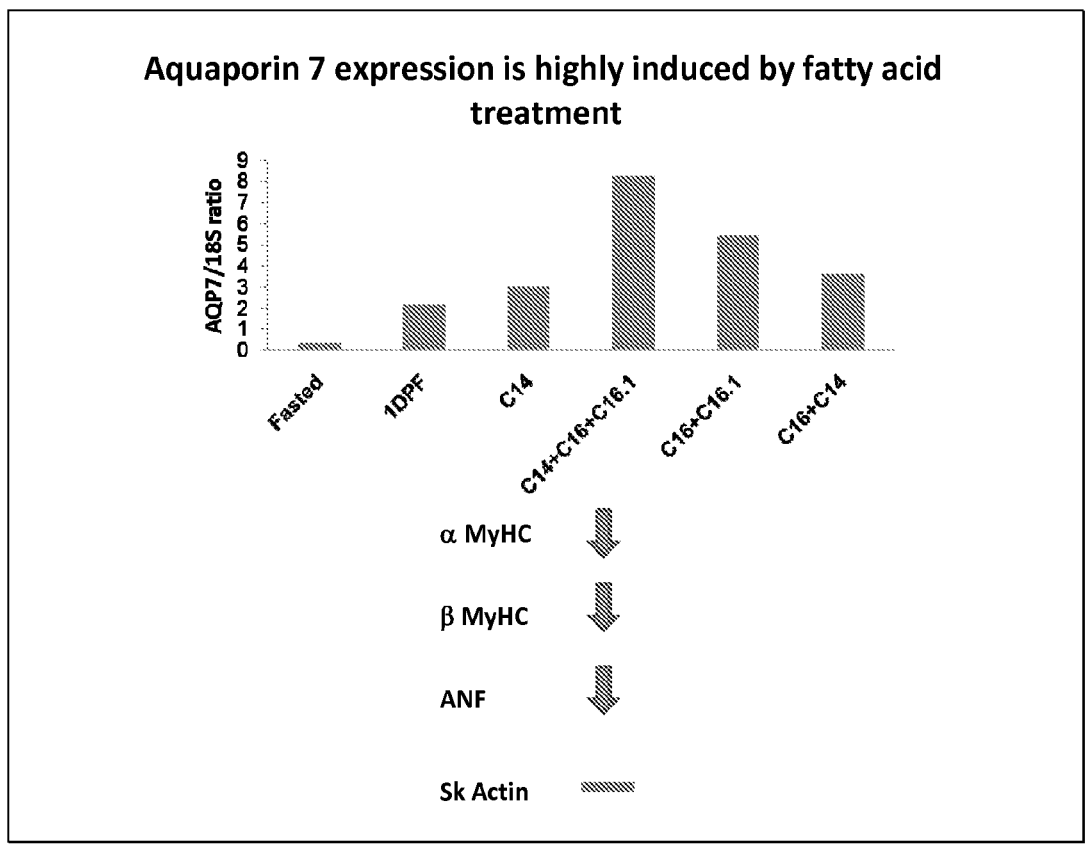
FIG. 11. Aquaporin 7 expression is highly induced by fatty acid treatment. Cardiomyoctes were evaluated for Aqp7 expression levels using fatty acid compositions.

In an effort to define genes activated in an in vitro model (neonatal rat cardiomyocytes treated with python plasma) a microarray analysis was performed on cells treated with fasted and fed python plasma. One of the genes that was highly up-regulated in cardiomyocytes that were fed plasma is aquaporin 7 (Aqp7), a transmembrane protein of the family of aqua/glycerol pore proteins. We have confirmed that Aqp7 is up-regulated on other animal models of physiologic hypertrophy such as exercise training and pregnancy in mice. On the contrary, Aqp7 is down-regulated on pathologic hypertrophy such as HCM transgenic mice. C14 and C16:1 were evaluated to determine if their induction of hypertrophy could also be responsible for the induction of Aqp7. To do so, cardiomyocytes cultured in the presence of fasted, fed and fasted supplemented with FFAs were analyzed by qPCR in order to quantitate changes in Aqp7 mRNA levels upon each experimental condition (FIG. 11). The addition of C14 induced Aqp7 mRNA only to comparable levels observed with 1 DPF plasma. However, the combination of C16, C14 and C16:1 exhibited the most significant effect, inducing Aqp7 four times higher than 1 DPF plasma.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,195
U.S. Pat. No. 4,683,202
U.S. Pat. No. 4,800,159
U.S. Pat. No. 5,206,347
U.S. Pat. No. 5,891,084
U.S. Pat. No. 6,669,716
U.S. Pat. No. 3,773,919
U.S. Pat. No. 4,439,196
U.S. Pat. No. 4,447,224
U.S. Pat. No. 4,447,233
U.S. Pat. No. 4,475,196
U.S. Pat. No. 4,486,194
U.S. Pat. No. 4,487,603
U.S. Pat. No. 4,554,101
U.S. Pat. No. 4,596,556
U.S. Pat. No. 4,790,824
U.S. Pat. No. 4,797,368
U.S. Pat. No. 4,941,880
U.S. Pat. No. 5,051,448
U.S. Pat. No. 5,064,413
U.S. Pat. No. 5,139,941

U.S. Pat. No. 5,169,862
U.S. Pat. No. 5,187,260
U.S. Pat. No. 5,270,163
U.S. Pat. No. 5,312,335
U.S. Pat. No. 5,383,851
U.S. Pat. No. 5,399,163
U.S. Pat. No. 5,475,096
U.S. Pat. No. 5,539,085
U.S. Pat. No. 5,559,103
U.S. Pat. No. 5,576,423
U.S. Pat. No. 5,582,981
U.S. Pat. No. 5,595,877
U.S. Pat. No. 5,637,459
U.S. Pat. No. 6,506,377
U.S. Pat. No. 7,192,951
U.S. Patent Publn. 20030147966
U.S. Patent Publn. 20030223938
U.S. Patent Publn. 2005/0197694
U.S. Patent Publn. 20050025709
U.S. Patent Publn. 20050143336
U.S. Patent Publn. 20050186290
U.S. Patent Publn. 20070009474
U.S. Patent Publn. 20070203083
U.S. Patent Publn. 20080221169
U.S. Patent Publn. 20080264102
Agre, J. Amer. Soc. Nephrol., 11:764-777, 2000.
Aksentijevich et al., Hum. Gene Ther., 7(9):1111-1122, 1996.
Almquiest et al., J. Med. Chem., 23:1392-98, 1980.
Andersen et al., Nature, 434:37-38, 2005.
Ausubel et al., In: Current Protocols in Molecular Biology, John, Wiley & Sons, Inc, NY, 1994; 1996.
Berge et al., J. Pharm. Sci., 66:1-19, 1977.
Blondelle et al., Biophys. J., 69:604-11, 1995.
Bosher and Labouesse, Nat. Cell. Biol., 2(2):E31-E36, 2000.
Ceperuelo-Mallafre et al., J. Clin. Endocrinol. Metab., 92(9):3640-5, 2007.
Chada et al., Mol. Ther., 7:S446, 2003.
Coffin, In: Virology, Fields et al. (Eds.), Raven Press, NY, 1437-1500, 1990.
Deen et al., Curr. Opin. Cell Biol., 10:435-442, 1999.
Duan et al., Circ. Res., 97:372-379, 2005.
Ecker and Crooke, Biotechnology, 13:351-69, 1995.
Elbashir et al., Genes Dev., 5(2):188-200, 2001.
EP 133,988
EP 143,949
EP 36,676
EP 58,481
EP 88,046
Eppstein et al., Proc. Natl. Acad. Sci. USA, 82:3688-3692, 1985.
Felgner et al., Proc. Natl. Acad. Sci. USA, 84(21):7413-7417, 1987.
Fire et al., Nature, 391(6669):806-811, 1998.
Fraley et al., Proc. Natl. Acad. Sci. USA, 76:3348-3352, 1979.
Freshney, In: Animal Cell Culture, A Practical Approach, $2^{nd}$ Ed., Oxford Press, UK, 1992.
Gabizon et al., Cancer Res., 50(19):6371-6378, 1990.
Ghosh and Bachhawat, In: Liver Diseases, Targeted Diagnosis and Therapy Using Specific Receptors and Ligands, Wu et al. (Eds.), Marcel Dekker, NY, 87-104, 1991.
Goodman and RO, In: Burger's Medicinal Chemistry And Drug Discovery, Vol. I, Wolff (Ed.), John Wiley & Sons, 1995.
Goodman and Shao, Pure Appl. Chem., 68:1303-08, 1996.
Grishok et al., Science, 287:2494-2497, 2000.
Hara-Chikuma et al., J. Biol. Chem., 280(16):15493-15496, 2005.
Harrison et al., Mol. Cell Biol., 24(24):10636-49, 2004.
Holladay et al., Tetrahedron Lett., 24:4401-04, 1983.
Hruby, Life Sci., 31:189-99, 1982.
Hudson et al., Int. J. Pept. Res., 14:177-185, 1979.
Inouye and Inouye, Nucleic Acids Res., 13:3101-3109, 1985.
Jennings-White et al., Tetrahedron Lett., 23:2533, 1982.
Kaneda et al., Science, 243:375-378, 1989.
Karlsson et al., EMBO J., 5:2377-2385, 1986.
Kato et al, J. Biol. Chem., 266:3361-3364, 1991.
Ketting et al., Cell, 99(2):133-141, 1999.
King et al., Molec. Med. Today, 6:60-65, 2000.
Langer et al., Chem. Tech., 12:98-105, 1982.
Langer et al., J. Biomed. Mater. Res., 15:167-277, 1981.
Lin and Avery, Nature, 402:128-129, 1999.
Liu et al., Cancer Res., 55(14):3117-3122, 1995.
Macejak and Sarnow, Nature, 353:90-94, 1991.
Mann et al., Cell, 33:153-159, 1983.
Montgomery et al., Proc. Natl. Acad. Sci. USA, 95:15502-15507, 1998.
Nicolas and Rubenstein, In: Vectors: A survey of molecular cloning vectors and their uses, Rodriguez and Denhardt, eds., Stoneham: Butterworth, pp. 494-513, 1988.
Nicolau and Sene, Biochim. Biophys. Acta, 721:185-190, 1982.
Nicolau et al., Methods Enzymol., 149:157-176, 1987.
Paskind et al., Virology, 67:242-248, 1975.
PCT Appln. PCT/US93/00829
PCT Appln. WO 98/07408
PCT Pub. Appln. 2005/120626
Pelletier and Sonenberg, Nature, 334(6180):320-325, 1988.
Remington's Pharmaceutical Sciences, 18th Ed. Mack Printing Co., 1289-1329, 1990.
Sambrook and Russell, Molecular Cloning: A Laboratory Manual $3^{rd}$ Ed., Cold Spring Harbor Laboratory Press, 2001.
Sambrook et al., In: Molecular cloning: a laboratory manual, $2^{nd}$ Ed., Cold Spring Harbor Laboratory Press, Cold Spring Harbor, N.Y., 1989.
Secor and Diamond, Nature, 395:659-62, 1998.
Secor et al., J. Exp. Biol., 203:2447-54, 2000.
Sharp and Zamore, Science, 287:2431-2433, 2000.
Sharp, Genes Dev., 13:139-141, 1999.
Sidman et al., Biopolymers, 22:547-556, 1983.
Smyth-Templeton et al., DNA Cell Biol., 21(12):857-867, 1997.
Solodin et al., Biochemistry, 34(41):13537-13544, 1995.
Spatola et al., Life Sci., 38:1243-49, 1986.
Tabara et al., Cell, 99(2):123-132, 1999.
Temin, In: Gene Transfer, Kucherlapati (Ed.), NY, Plenum Press, 149-188, 1986.
Templeton et al., Nat. Biotechnol., 15(7):647-652, 1997.
Thierry et al., Proc. Natl. Acad. Sci. USA, 92(21):9742-9746, 1995.
Tsukamoto et al., Nat. Genet., 9(3):243-248, 1995.
Waspe et al., J. Clin. Invest., 85(4):1206-14, 1990.
Wong et al., Gene, 10:87-94, 1980.
Yang and Huang, Gene Therapy, 4 (9):950-960, 1997.
Zhu et al., Science, 261(5118):209-211, 1993.

What is claimed is:

1. A method for inducing physiologic hypertrophy in cardiac cells comprising administering to the cardiac cells an effective amount of a pharmaceutical composition comprising an isolated or purified fatty acid composition, wherein the fatty acid composition consists of a combination of myristic acid, palmitic acid, and palmitoleic acid fatty acid (MPP fatty acids), wherein the composition comprises no other fatty acids, and wherein the ratio of myristic to palmitic acid is about 1:2 to about 1:3, and the ratio of myristic to palmitoleic acid is about 1:0.1 to about 1:0.2.

2. The method of claim 1, wherein the composition is formulated for administration to a human patient.

3. The method of claim 2, wherein the composition is formulated for administration to the patient orally or intravenously.

4. The method of claim 2, wherein the composition is formulated as a tablet, capsule, or lozenge.

5. The method of claim 4, wherein the composition is formulated for delayed or extended release.

6. The method of claim 2, wherein the patient is determined to be at risk for a cardiovascular disease or cardiovascular condition.

7. The method of claim 2, wherein the patient exhibits one or more symptoms of a cardiovascular disease or cardiovascular condition.

8. The method of claim 2, wherein the patient has one or more risk factors associated with a cardiovascular disease or cardiovascular condition.

9. The method of claim 2, wherein the patient has been diagnosed with a cardiovascular disease or cardiovascular condition.

10. The method of claim 9, wherein the cardiovascular disease or cardiovascular condition is one or more of hypertension, aneurysm, angina, atherosclerosis, cerebrovascular accident, cerebrovascular disease, peripheral vascular disease, cardiac fibrosis, coronary artery disease, myocardial infarction, arrhythmia, or congestive heart failure.

11. The method of claim 1, wherein the cardiac cells are human cardiac cells.

* * * * *